United States Patent
Baska

(10) Patent No.: US 7,997,274 B2
(45) Date of Patent: Aug. 16, 2011

(54) LARYNGEAL MASK

(75) Inventor: Kanag Baska, Strathfield (AU)

(73) Assignee: Meenakshi Baska, Strathfield, New South Wales (AU), part interest ( * ) Notice: Subject to any disclaimer, the term of this patent is extended or adjusted under 35 U.S.C. 154(b) by 1242 days.

(21) Appl. No.: 11/344,895

(22) Filed: Jan. 31, 2006

(65) Prior Publication Data

US 2006/0180156 A1   Aug. 17, 2006

Related U.S. Application Data

(63) Continuation of application No. PCT/AU2004/001011, filed on Jul. 30, 2004.

(30) Foreign Application Priority Data

Aug. 1, 2003 (AU) .............................. 2003904025
Feb. 20, 2004 (AU) .............................. 2004900835

(51) Int. Cl.
A61M 16/00 (2006.01)
A62B 9/06 (2006.01)

(52) U.S. Cl. ................................................. 128/207.14

(58) Field of Classification Search ............. 128/204.17, 128/200.26, 207.14–16
See application file for complete search history.

(56) References Cited

U.S. PATENT DOCUMENTS

| | | | | |
|---|---|---|---|---|
| 4,198,970 A * | 4/1980 | Luomanen | | 128/207.15 |
| 4,995,388 A * | 2/1991 | Brain | | 128/207.15 |
| 5,038,766 A * | 8/1991 | Parker | | 128/200.26 |
| 5,241,956 A * | 9/1993 | Brain | | 128/207.15 |
| 5,623,921 A * | 4/1997 | Kinsinger et al. | | 128/200.26 |
| 6,079,409 A * | 6/2000 | Brain | | 128/200.26 |
| 6,119,695 A * | 9/2000 | Augustine et al. | | 128/207.15 |
| 6,390,093 B1 * | 5/2002 | Mongeon | | 128/207.15 |
| 6,422,239 B1 * | 7/2002 | Cook | | 128/207.15 |
| 6,439,232 B1 * | 8/2002 | Brain | | 128/207.15 |
| 6,546,931 B2 | 4/2003 | Lin | | 128/207.15 |
| 6,689,062 B1 * | 2/2004 | Mesallum | | 600/439 |
| 6,705,318 B1 | 3/2004 | Brian | | 128/207.14 |
| 7,204,252 B2 * | 4/2007 | Johnson | | 128/207.15 |
| 2002/0014238 A1 * | 2/2002 | Kotmel | | 128/204.18 |
| 2003/0051734 A1 * | 3/2003 | Brain | | 128/207.15 |
| 2004/0020491 A1 * | 2/2004 | Fortuna | | 128/207.15 |
| 2005/0081861 A1 | 4/2005 | Nasir | | 128/207.14 |
| 2006/0201516 A1 | 9/2006 | Petersen et al. | | 128/207.14 |
| 2006/0207601 A1 | 9/2006 | Nasir | | 128/207.14 |

FOREIGN PATENT DOCUMENTS

| | | |
|---|---|---|
| JP | 2-283378 | 11/1990 |
| WO | WO 94/02191 | 2/1994 |
| WO | WO 00/09189 | 2/2000 |
| WO | WO 02/32490 A2 | 4/2002 |
| WO | WO 2004/016308 A2 | 2/2004 |

* cited by examiner

*Primary Examiner* — Justine R Yu
*Assistant Examiner* — Colin Stuart
(74) *Attorney, Agent, or Firm* — Winston & Strawn LLP

(57) ABSTRACT

A device for maintaining an airway in a patient. This device includes a mask having a resilient conformable peripheral portion that is shaped such that the mask forms a seal with the larynx when the mask is positioned in the laryngo pharynx to thereby prevent ingress of extraneous fluids into the larynx. The peripheral portion of the mask define at least one cavity for providing fluid communication to the esophagus when the mask is inserted into the laryngo pharynx. An airway tube is connected to or formed with the mask for passing gas to the larynx when the mask is properly inserted into the laryngo pharynx. The airway tube preferably is curved as it leaves the mask.

25 Claims, 21 Drawing Sheets

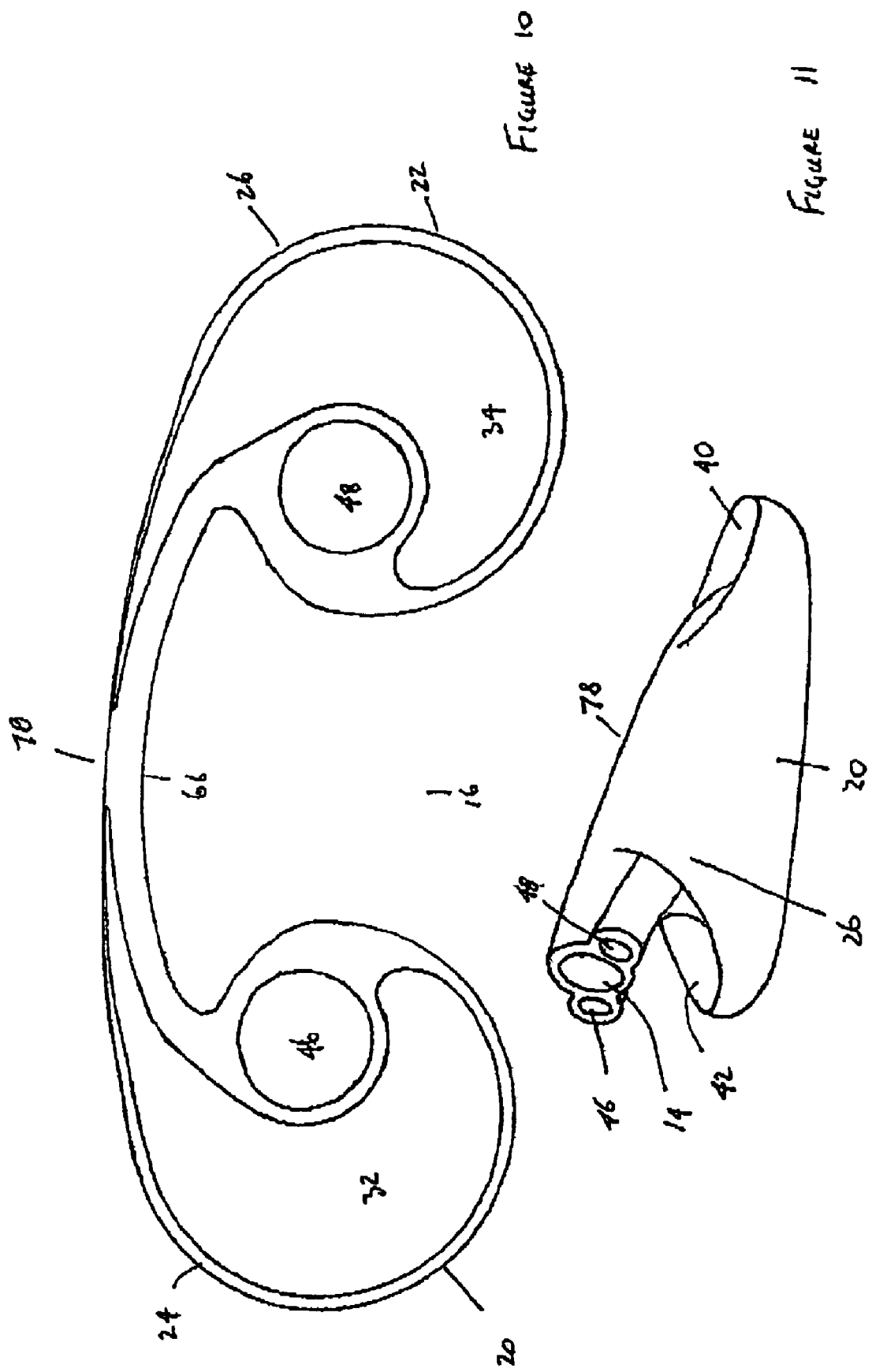

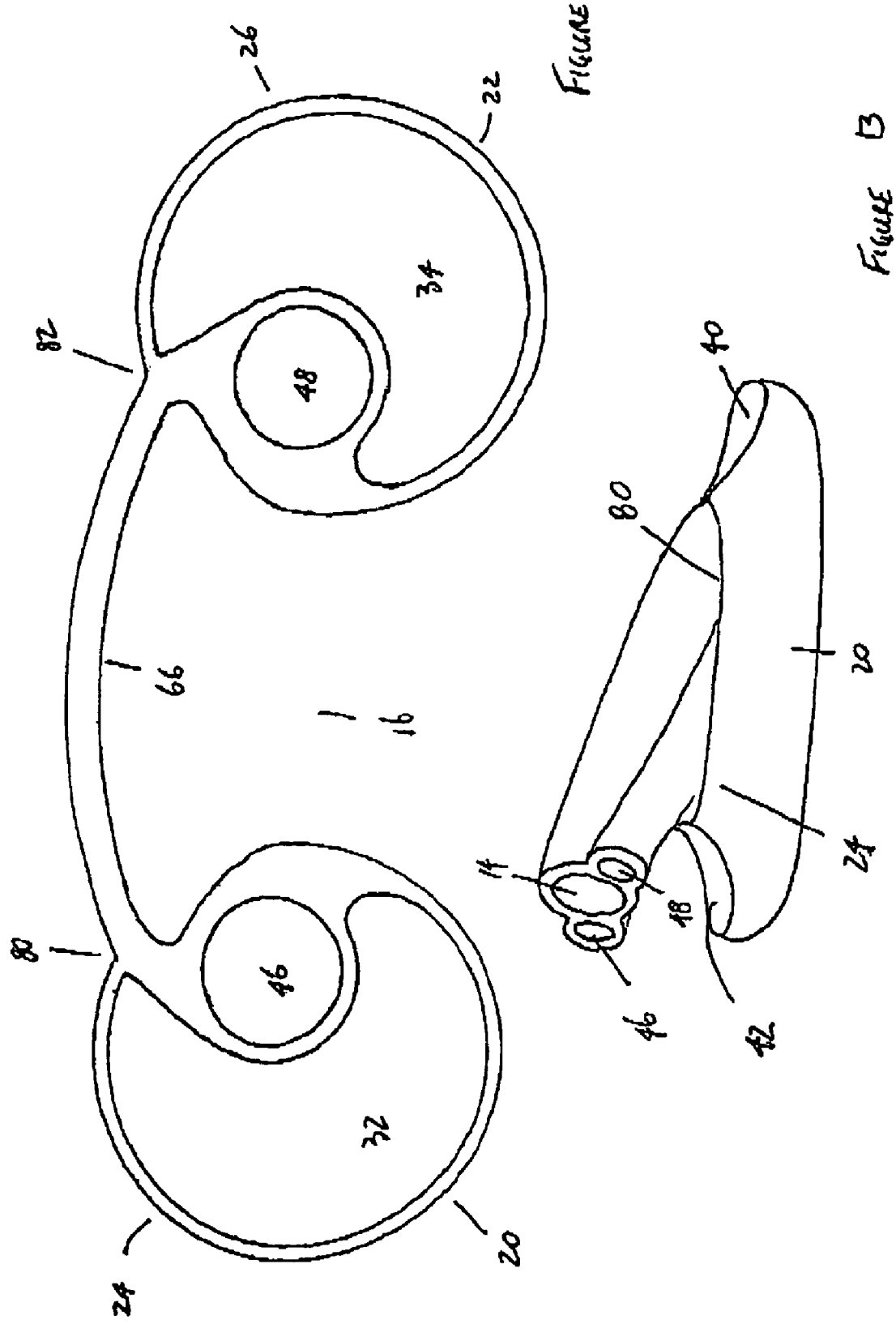

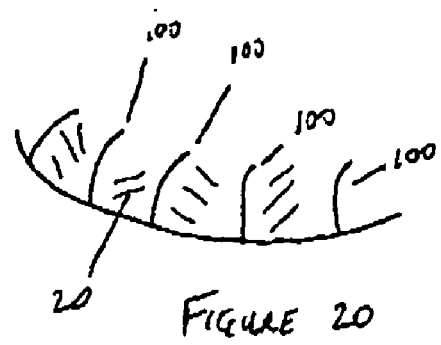
FIGURE 20
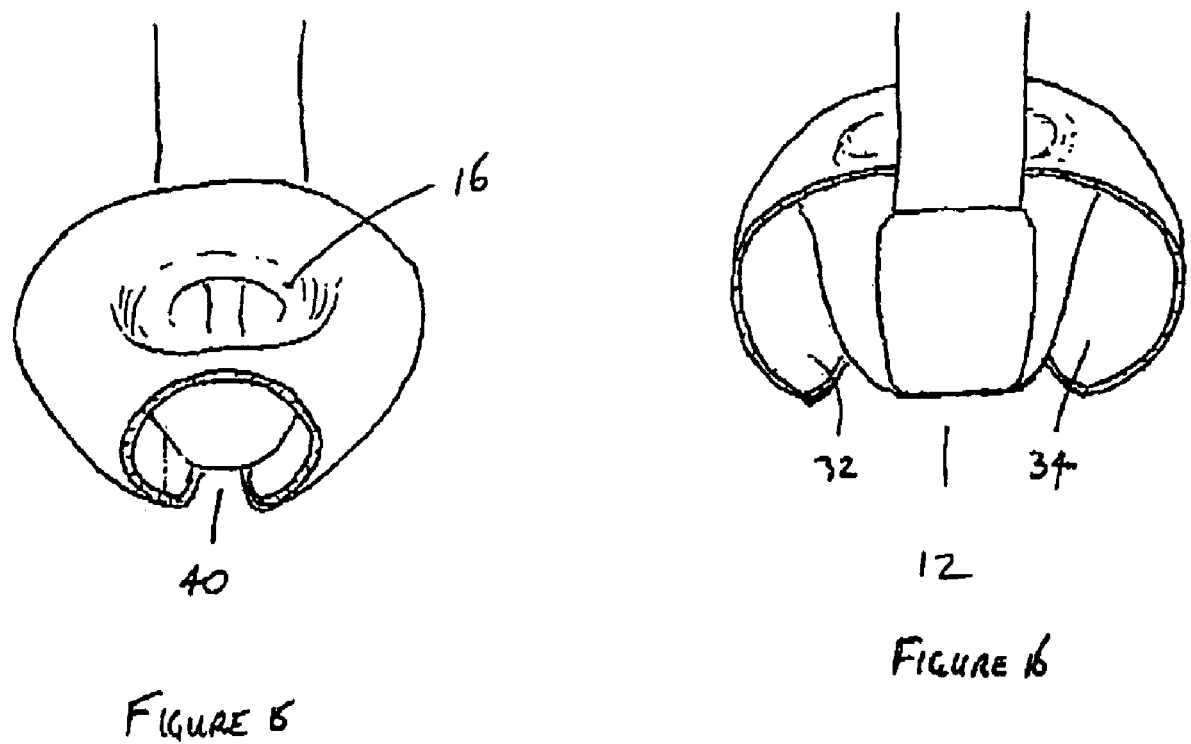
FIGURE 15
FIGURE 16

SECTION B-B

LARYNGEAL MASK

CROSS-REFERENCE TO RELATED APPLICATIONS

This application is a continuation of International application PCT/AU2004/001011 filed Jul. 30, 2004, the entire content of which is expressly incorporated herein by reference thereto.

FIELD OF THE INVENTION

The present invention relates to a device for maintaining an airway in a patient. In preferred embodiments, the present invention relates to a laryngeal mask.

BACKGROUND OF THE INVENTION

Maintenance of a viable airway is critical to patient safety during surgical procedures conducted under general anesthetic. Maintenance of a viable airway during such surgical procedures had, for many years, been achieved by insertion of an endo-tracheal tube into the patient. The endo-tracheal tube was typically inserted through the oral cavity or nasal cavity, into the larynx, through the vocal cord and into the trachea. As the endo-tracheal tube had to be inserted through the vocal cords, difficulty was often experienced in correctly positioning the endo-tracheal tube.

British patent no. 2,111,394 (which corresponds to U.S. Pat. No. 4,509,514) describes a device for maintaining an airway in a patient. The device is described as being an artificial airway device. The device comprises a curved, flexible tube opening at one end into the interior of a hollow mask portion shaped to conform to fit readily into the actual and potential space behind the larynx and to seal around the circumference of the laryngeal inlet without penetrating into the interior of the larynx. Commercial forms of this device have an inflatable collar extending around the periphery of the mask. The inflatable collar is adapted to form the seal around the laryngeal inlet when the collar is inflated. Additionally, the mask portion included an inflatable posterior part which is adapted to press against the back of the throat and thereby increase the sealing pressure around the laryngeal inlet.

British patent no. 2,111,394 states that the shape and (when fitted) the inflatable part or parts of the mask ensure that it approximates closely to the shape of the space between the laryngeal inlet and the walls of the lower part of the throat behind it. Since the walls of tissue forming the back of the throat are relatively rigid, inflation of the mask forces it more tightly against the tissues surrounding the laryngeal inlet, so forming an airtight seal, while tending to anchor the mask in position.

In use of the device described in GB 2,111,394, the device is inserted through the mouth of the patient and down the throat past the epiglottis until the mask comes to rest with its distal end in the base of the throat, lying against the upper end of the normally closed esophagus. The inflatable ring on the mask is then inflated to seal around the inlet to the larynx. The patent's airway in thus secure and unobstructed and the laryngeal mask can be connected directly to conventional anesthetic circuit hosing for either positive pressure or spontaneously breathing.

When a patient is placed under general anesthetic, the patient is frequently lying in the horizontal position on his or her back or side. When under general anesthetic, reflex response in the body is suppressed and the sphincter closing the top of the stomach from the esophagus is relaxed. Consequently, gastric juices (which are acidic in nature) can flow along the esophagus. It is important to ensure that such gastric juices do not enter the trachea as aspiration of gastric juices into the lungs can have potentially fatal consequences.

Similarly, where a patient under general anesthetic is undergoing a surgical procedure of the nose, mouth or throat (e. g. a tonsillectomy, endoscopic nasal surgery), saliva, blood and nasal secretions can travel down through the pharyngo larynx and into the trachea and thereafter into the lungs. Again, this is a potentially dangerous situation.

When using a laryngeal mask such as the one described in British patent no. 2,111,394, the present inventor has found that if significant volumes of gastric juices collect around the mask the gastric juices can work their way past the seal of the mask and into the larynx. This is dangerous if the gastric juices and acid gets into the lungs.

The laryngeal mask described in British patent no. 2,111,394 may also have problems of leakage occurring in the inflatable ring or collar, due to a faulty valve in the pilot line or due to leakage or tearing of the inflatable ring or collar. It is apparent that deflation of the cuff substantially increases the chance that the seal around the larynx will be lost, which consequently increases the possibility of gastric acids getting into the lungs. Even in normal use without cuff deflation, there remains a possibility that a gush of acid from the stomach can get around the cuff and enter the air passage as there is no other way for the acid to escape (due to the cuff totally blocking the laryngopharynx). The presently available masks also have the limitation that they cannot be used safely on all patients, especially patients with a large abdomen.

In order to minimize the likelihood of the abovementioned problems, the patentee of British patent no. 2,111,394 introduced a laryngeal mask that had a double cuff to produce a total seal around the area of the larynx. This mask also included an additional tube that extends along the back of the laryngeal mask and extends into the esophagus. This allows gastric acid to be sucked out from the stomach by way of a Ryles tube inserted through this passage. It has been found that applying suction to the esophageal tube of this laryngeal mask can cause the tissue of the esophagus to be sucked into the inlet of the second tube. This results in the second tube becoming blocked, thereby preventing removal of gastric acids.

The double cuff laryngeal mask also includes two small additional tubes that open into the larynx-side of the mask. These tubes can be used to remove from the larynx any gastric juices that make their way past the seal into the larynx.

However, applying suction to these tubes raises the possibility of removing anesthetic gases from the trachea and increases the possibility of collapsing the lung or lungs. Successful removal of all the volume of acid coming up from the stomach is also not possible. Consequently, the acid may preferably move into the large diameter airway (trachea) due to the large diameter of the airway providing a path of lower resistance to fluid flow than the smaller diameter opening in the mask.

The improved laryngeal mask described above is described in Australian patent no. 630433. Despite those improvements, further enhancements and modifications are needed, and these are now provided by he present invention.

SUMMARY OF THE INVENTION

In its most general form, the present invention relates to a device for maintaining an airway in a patient comprising a mask, the mask having a resilient conformable peripheral portion shaped such that the mask forms a seal with the larynx when the mask is positioned in the laryngo pharynx to thereby prevent ingress of extraneous fluids into the larynx, the peripheral portion of the mask defining at least one cavity for providing fluid communication to the esophagus when the mask is inserted into the laryngo pharynx, and an airway tube connected to or formed with the mask for passing gas to the larynx when the mask is properly inserted into the laryngo pharynx.

In a first aspect, the present invention provides a device for maintaining an airway in a patient comprising a mask, the mask having a resilient conformable peripheral portion shaped such that the mask forms a seal with the larynx when the mask is positioned in the laryngo pharynx to thereby prevent ingress of extraneous fluids into the larynx, the peripheral portion of the mask defining at least one cavity for providing fluid communication between the laryngo pharynx and the esophagus when the mask is inserted into the laryngo pharynx, and an airway tube connected to or formed with the mask for passing gas to the larynx when the mask is properly inserted into the laryngo pharynx.

Preferably, the peripheral portion of the mask comprises an upturned edge, the upturned edge defining the at least one cavity. Alternatively, the peripheral portion of the mask includes a wall portion that extends from a lateral edge of the mask away from the laryngeal side of the mask and inwardly relative to the outer edge of the mask. The wall portion suitably extends along a part of at least one lateral edge of the mask. The wall portion may include a further inner portion that extends away from the lateral edge of the mask and towards the laryngeal side of the mask.

The peripheral portion may include a fold back portion folding back over the peripheral portion to thereby form the at least one cavity, the fold back portion extending along a part of at least one lateral edge of the mask.

Preferably, the at least one cavity comprises two cavities extending along opposed edges of the mask. In another embodiment, the cavity is formed by one or more channels formed in or forming part of the peripheral portion of the mask. Preferably, the one or more channels have open ends that blend into an upturned edge of the peripheral portion of the mask.

The mask, when properly inserted, has a laryngeal side and a laryngo pharynx side. Preferably, the laryngo pharynx side is provided with a contact member for contacting a wall of the laryngo pharynx, the contact member assisting in spacing of the peripheral portion of the mask from the laryngo pharynx wall to thereby facilitate formation of a seal with the larynx.

The contact member may comprise a hood connected to or formed with the mask. The hood may have edges that extend over the peripheral portion of the mask. Alternatively, the contact member may comprise one or more projections extending away from the laryngeal side of the mask. Indeed, the contact member may comprise any surface positioned on the laryngo pharynx side of the mask that contacts the wall of the laryngo pharynx when the mask is properly inserted.

The mask may further include at least one fluid tube opening into the at least one cavity, the at least one fluid tube extending away from the mask, the at least one fluid tube being adapted to remove fluids from the laryngo pharynx side of the mask, in use. In one embodiment, the at least one fluid tube has a distal outlet located within the periphery of the mask.

More preferably, the mask is provided with two fluid tubes in fluid communication with the at least one cavity. One tube may have a source of suction attached to it to remove fluids, such as gastric juices, blood or nasal secretions, from the laryngo pharynx side of the mask and the other tube may be provided for admitting air from the atmosphere to the laryngo pharynx side of the mask. In this fashion, fluids can be removed from the laryngo pharynx side of the mask by use of external suction. By virtue of the mask having a second fluid tube for admitting air from the atmosphere to the laryngo pharynx side of the mask, the level of suction does not build up to such an extent that the wall of the laryngo pharynx or the wall of the esophagus is sucked into the at least one cavity.

It will be appreciated that the fluid tubes should be of sufficient length to enable them to be connected to a source of vacuum or a source of venting air.

Preferably, the fluid tubes are sufficiently long such that the proximal ends thereof are positioned externally to the mouth of the patient when the mask is properly inserted.

The mask further includes an airway tube connected to or formed with the mask for passing gas to the larynx when the mask is inserted into the laryngo pharynx. The laryngeal side of the mask preferably defines a depression and the airway tube is preferably in fluid communication with this depression. The airway tube may be flexible tube or it may be a rigid tube that is shaped to facilitate insertion and positioning of the mask in the laryngo pharynx.

The depression on the laryngeal side of the mask may be defined by an inner wall of the mask and the inner wall preferably has a region of relative increased width and a region of relative decreased width such that the region of relative increased width defines a recess in the depression when the mask is inserted, the recess providing a region of clearance between the inner wall and the epiglottis of the patient. In this embodiment, the epiglottis cannot block the depression even if the mask is inserted in a fashion that causes the epiglottis to be down turned. Thus, the epiglottis cannot block the flow of air to the laryngeal side of the mask.

Suitably, the inner wall of the mask is arranged to facilitate maintenance of the depth of the airway depression and to maintain pressure against the surrounding areas of the larynx to maintain the seal against ingress of gastric juices into the larynx and to allow positive pressure ventilation of the airway. A combination of the resilience of the inner wall and the dimensions of the inner wall are used to obtain these effects.

In a preferred embodiment of the present invention, the distal portion of the mask includes a longitudinally extending portion that, in use, extends into the esophagus, the longitudinally extending portion being in fluid communication with the at least one cavity. Preferably, the longitudinally extending portion extends into an upper portion of the esophagus.

Preferably, the longitudinally extending portion is shaped to bias a distal end of the at least one cavity to an open position.

The longitudinally extending portion may comprise a passageway having an opening along an upper part thereof. In this regard, the side walls of the passageway may extend towards each other but not be connected to each other at their respective upper ends. In this fashion, the longitudinally extending portion can be collapsed inwardly to facilitate insertion of the mask into the patient and, once in position, open up again.

In another embodiment, the longitudinally extending portion comprises a tubular portion.

The longitudinally extending portion may comprise a concertina portion that can be folded up or collapsed to facilitate insertion of the mask into a patient and to move to an expanded position once inserted. The concertina portion may have plurality of ribs. Alternatively, the concertina portion may comprise a corrugated tube. As a further alternative, the longitudinally extending portion may include a plurality of fold lines.

The longitudinally extending portion may be integrally formed with the mask or it may be joined to the mask. The longitudinally extending portion may be a longitudinal extension of the peripheral portion of the mask. The longitudinally extending portion may be joined to the peripheral portion of the mask. Alternatively, it may be joined to an upper part of the mask.

In order to facilitate insertion of the mask into a patient, the proximal tubing of the mask may be shaped to have a curvature extending from near the proximal end of the mask and in a direction away from the mask.

The mask may have an airway tube that is shaped such that it includes a section that curves towards the laryngeal side of the mask. Preferably, the device of the second aspect of the invention has an airway tube that curves downwardly towards the laryngeal side of the mask at a region located adjacent a proximal end of the mask. In this embodiment, insertion of the mask is much easier as the curvature of the tubing tends to move the mask into the airway and towards the larynx without necessarily requiring external guidance by the anesthetist placing his or her fingers in close proximity to or in contact with the mask, which is commonly required with conventional laryngeal masks.

In a second aspect, the present invention provides a device for maintaining an airway in a patient comprising a mask, the mask having a resilient conformable peripheral portion shaped such that the mask forms a seal with the larynx when the mask is positioned in the laryngo pharynx to thereby prevent ingress of extraneous fluids into the larynx, a first tube having a outlet at a distal end thereof, the outlet of the first tube being in fluid communication with the esophagus when the mask is in use, a second tube having an opening at a distal end thereof, the opening of the second fluid tube being separate to the opening of the first tube, the opening of the second fluid tube being in fluid communication with the esophagus when the mask is in use, the first fluid tube adapted to remove fluids from the laryngo pharynx side of the mask in use, the second fluid tube adapted to provide venting fluid to the laryngo pharynx side of the mask in use and an airway tube connected to or formed with the mask for passing gas to the larynx when the mask is properly inserted into the laryngo pharynx.

BRIEF DESCRIPTION OF THE DRAWINGS

Preferred embodiments of the present invention will now be described with reference to the following drawings in which:

FIG. 10 shows a further cross-sectional view of another embodiment of the invention;

FIG. 11 is a side view of the device shown in FIG. 10;

FIG. 12 is a cross-sectional view that is similar to that shown in FIG. 10 but of yet a further embodiment of the present invention;

FIG. 13 is a side view of the device shown in FIG. 12;

FIG. 15 is a front view of a device in accordance with the present invention showing its shape when inserted into the laryngo pharynx;

FIG. 16 is a rear view of the device shown in FIG. 15;

FIG. 20 is a fragmentary view which shows the lower part of the outer periphery of the mask for another embodiment of the present invention;

DETAILED DESCRIPTION OF THE PREFERRED EMBODIMENTS

It will be understood that the attached drawings are provided to show preferred embodiments of the invention. It is to be understood that the invention should not be considered to be limited to all of the features shown in those drawings.

Referring now to FIGS. 1 to 6, which show various views of the device 10 in accordance with the present invention, it can be seen that the device 10 includes a mask 12. An airway tube 14 is connected to or formed with the mask such that the distal end of the airway tube opens into the airway cavity 16 that is formed on the laryngeal side of the mask. The airway tube 14 may be a soft, flexible tube.

Alternatively, it may be a rigid tube that has been shaped to facilitate insertion and positioning of the device into the proper position in the patient. Airway tube 14 enables gases to be provided to the larynx and trachea when the device has been properly inserted into the patient. The gas that is provided to the larynx and trachea may comprise anesthetic gases, oxygen enriched gases or an active ventilating gas.

Figure 6:
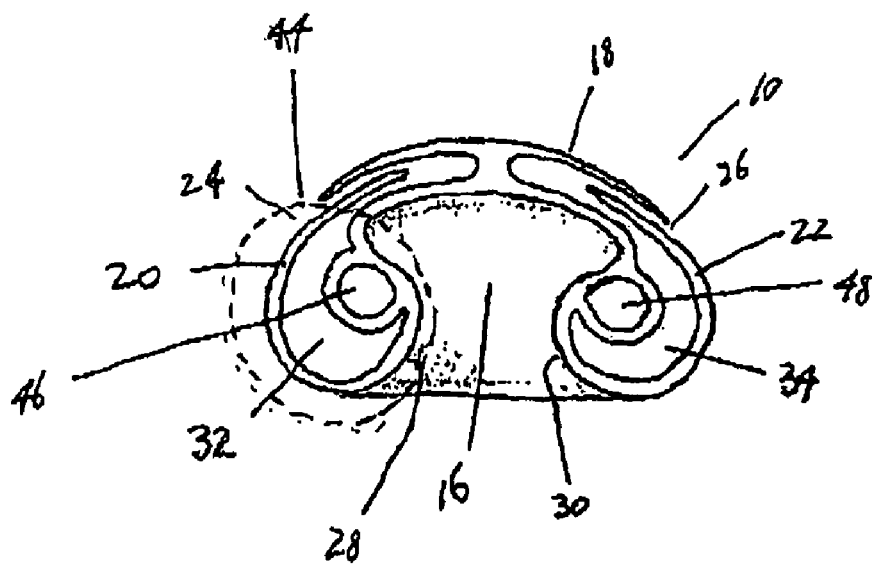
FIG. 6 is a cross-sectional view taken along A-A in FIG. 3.

The laryngo pharynx side of the mask includes an upper surface in the form of a hood 18. Throughout this specification, the term "upper" will be used to refer to the laryngo pharynx side of the mask and the term "lower" will be used to refer to the laryngeal side of the mask. The laryngo pharynx side of the mask also includes upturned side walls 20,22. As best seen in FIG. 6, upturned side walls 20, 22 include a wall portion that extends from an outer most edge of the mask 12. These wall portions extend in a direction that is away from the laryngeal side of the mask and towards the inner part of the mask. These wall portions are designated in FIG. 6 by reference numerals 24 and 26.

As can best be seen from FIG. 6, the lower walls 28,30 continue outwardly to the outermost edge of the mask and then continue upwardly into wall portions 24,26. Accordingly, the wall portions 24,26, together with the inner wall of the airway cavity 16 define cavities 32,34. For convenience, cavities 32,34 will hereinafter be referred to as "fluid cavities".

As best shown in FIGS. 1,2, 3 and 5, upturned side walls 20,22 of the upper part of the mask are significantly lower at the longitudinal ends 36,38 of the mask. This can perhaps be described by saying that the wall portions 24,26, which constitute the upper wall portions of the upturned side walls 20,22, do not continue into the longitudinal extremities of the mask. In this fashion, an opening or space 40 is provided at the distal end of the mask 12. Similarly, an opening 42 is provided at the proximal end of the mask 12. The openings 40,42 are in fluid communication with the fluid cavities 32,34. In this manner fluids can flow from the distal end 40 to the proximal end 42 of the mask via opening 40, fluid cavities 32,34 and opening 42. Similarly, a gastric tube or other tube may be passed through opening 42, via one of fluid cavities 32,34, through opening 40 and inserted into the esophagus of a patient to reach the stomach. The fluid cavities 32,34 are in fluid communication with each other.

Figure 2:
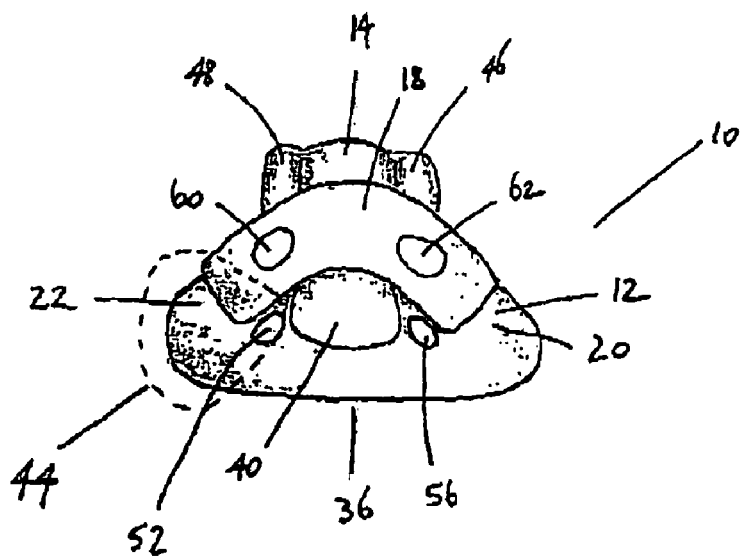
FIG. 2 is a front view of the device shown in FIG. 1.
Figure 3:
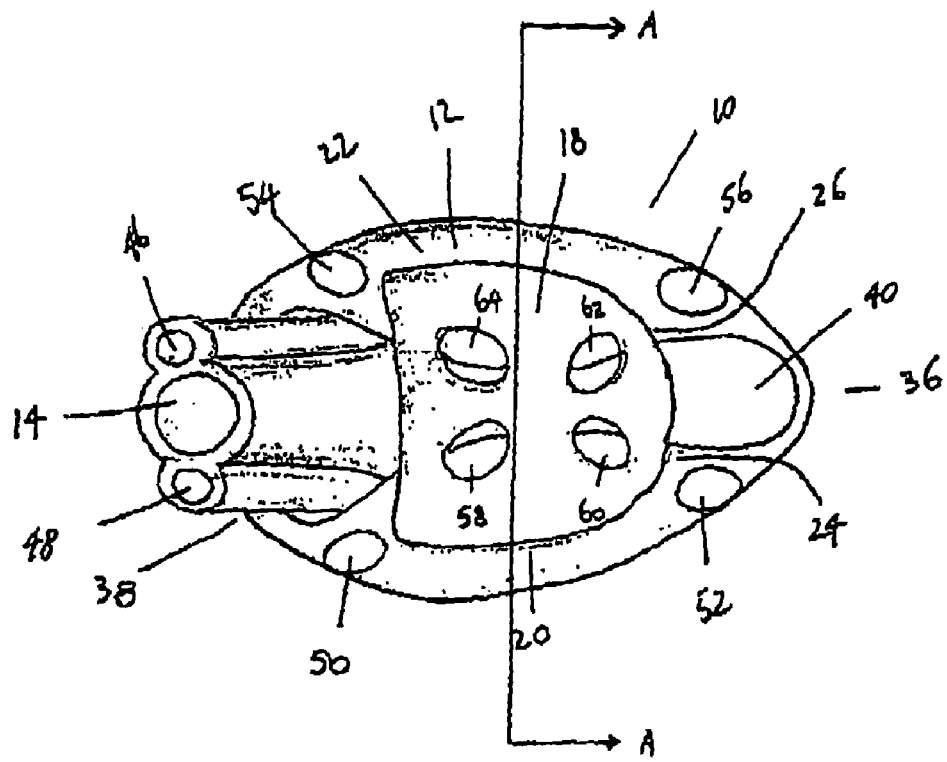
FIG. 3 is a view from above of the device shown in FIG. 1.
Figure 4:
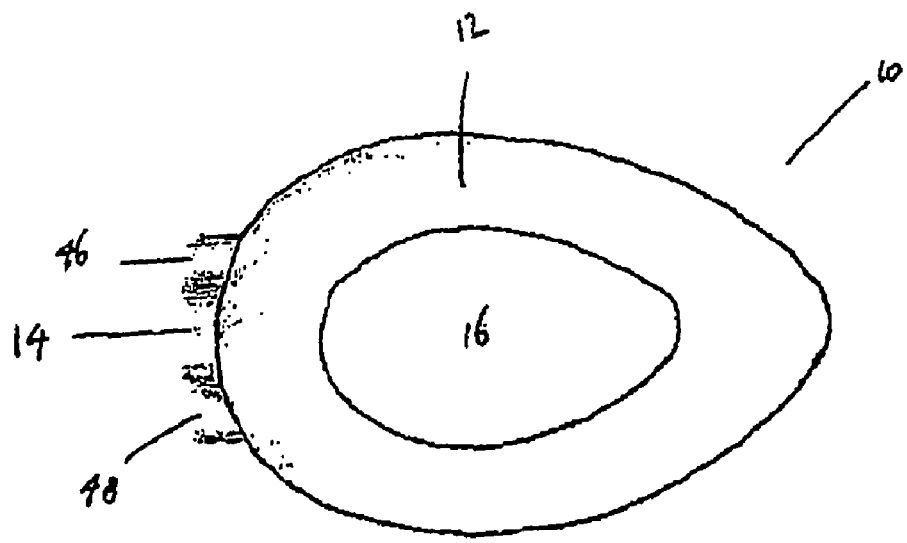
FIG. 4 is a view from underneath of the device shown in FIG. 1.
Figure 5:
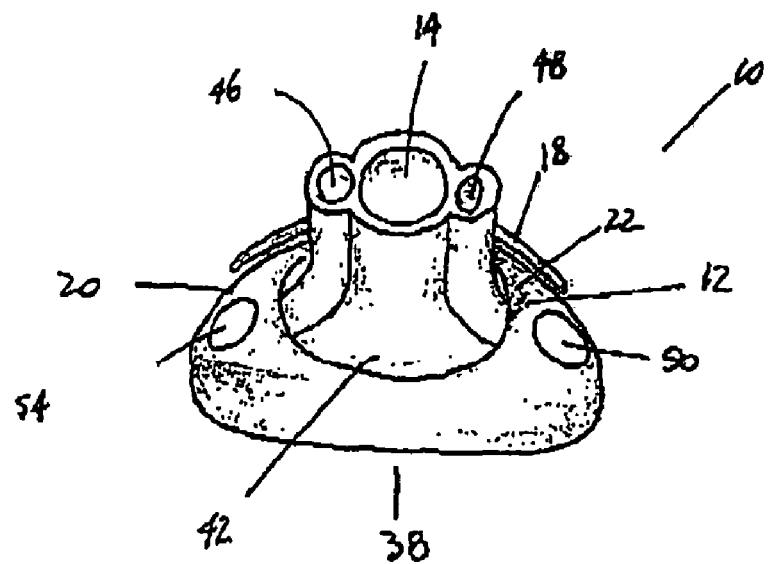
FIG. 5 is a rear view of the device shown in FIG. 1.

FIGS. 2 and 6 show a region 44 delineated by a dotted section.

Region 44 may be considered to comprise the peripheral portion of the mask. It will be appreciated that the peripheral portion 44 is a resilient, conformable portion that is shaped such that the mask forms a seal with the larynx when the mask is properly positioned in the laryngo pharynx of the patient. The peripheral portion also defines fluid cavities 32,34 and openings 40,42 to thereby allow fluid communication between the laryngo pharynx and the esophagus when the mask is properly inserted into the laryngo pharynx.

The device 10 shown in FIGS. 1 to 6 is also provided with two fluid tubes 46,48. Fluid tubes 46,48 open at their distal end into fluid cavities 32,34. In this fashion, any fluid that has collected in fluid cavities 32,34 can be removed by suction applied to one or both of fluid tubes 46,48. It is especially preferred that one of fluid tubes 46,48 is attached to a source of suction and the other of fluid tubes 46, 48 is either attached to a source of positive pressure gas or simply allowed to vent to the atmosphere. In that way, when suction is applied to one of fluid tubes 46,48, air flows down the other of tubes 46,48 to thereby prevent the build up of suction in the vicinity of the upper side of the mask whilst still allowing fluid to be withdrawn from the upper side of the mask. This feature assists in preventing the soft tissue of the esophagus and the laryngo pharynx being sucked into and blocking the opening 40 or fluid cavities 32,34, which would stop the removal of fluid from the upper side of the mask.

The peripheral portion of the mask, in particular, the wall portions 24, 26 may be provided with additional holes 50,52, 54,56 in order to enhance the efficiency of removal of fluid from the upper side of the mask when in use. The additional holes may be of any shape and of any desired size. The number, size and shape of the holes may vary without departing from the scope of the present invention.

The hood 18 may also be provided with holes 58,60, 62,64. In use, a lubricant may be put into those holes in order to assist in putting the mask into position. The holes in the hood may also allow the wall portions of the peripheral portion of the mask to move more freely with the hood and floor.

Finally, with regard to FIGS. 1 to 6, it will be appreciated that airway tube 14 and fluid tube 46,48 are shown in a truncated form. In the actual device, the airway tube 14 and fluid tubes 46,48 are significantly longer than shown in FIGS. 1 to 6. This is more clearly shown in FIG. 7.

Figure 7:
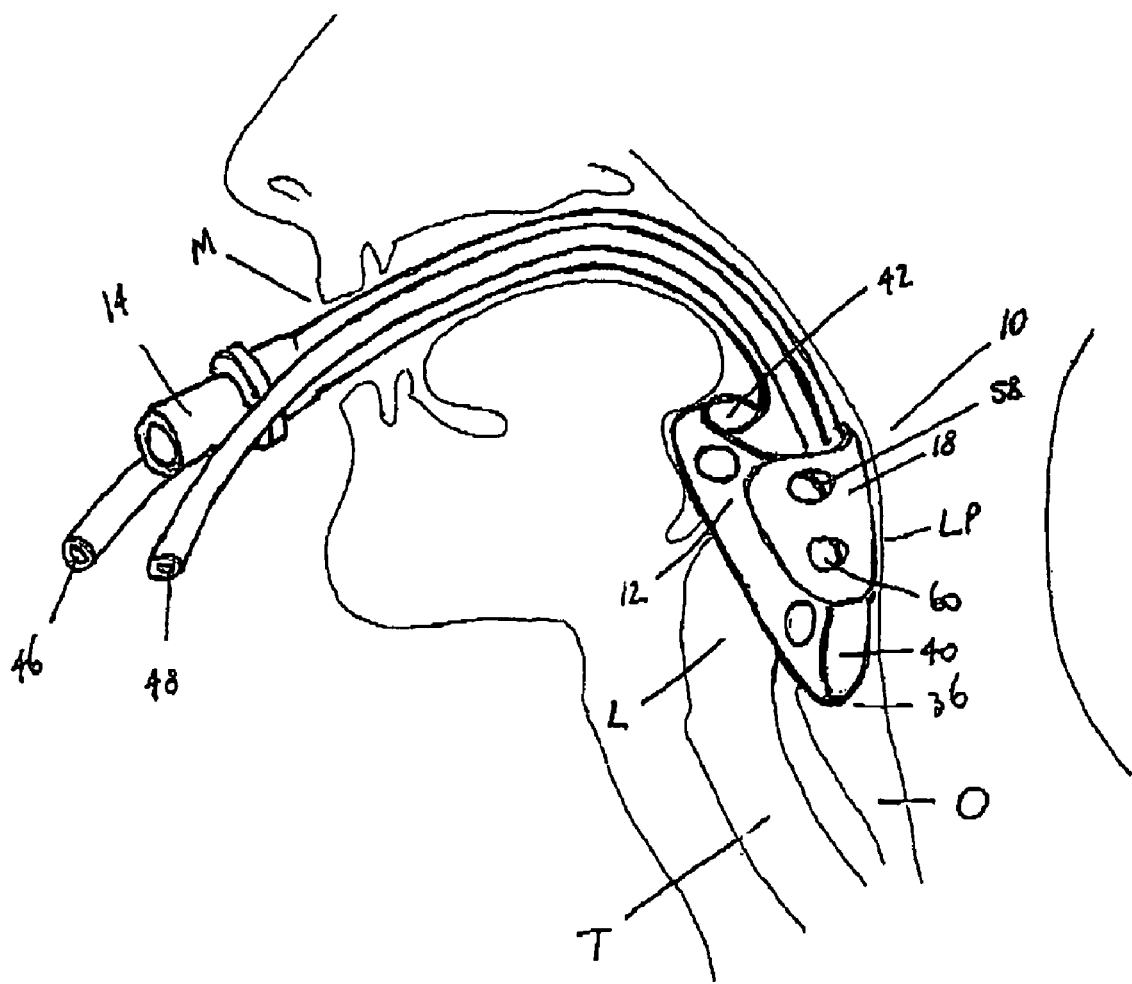
FIG. 7 is a cross-sectional view of a device in accordance with the present invention properly inserted into the laryngo pharynx of a patient.

Turning now to FIG. 7, which shows the device 10 properly inserted into the laryngo pharynx LP of patient, it can be seen that the airway tube 14 and fluid tube 46,48 are of sufficient length that they extend out of the mouth M of patient.

The airway tube 14 may be provided with a connector at its proximal end to enable it to be connected to a source of gases, such as anesthetic gases. The fluid tubes 46,48 may be provided with appropriate connectors to enable one or both of them to be connected to a source of vacuum. However, as indicated above, it is preferred that only one of the fluid tubes 46,48 be connected to a source of vacuum whilst the other is simply allowed to vent atmospheric gases to the laryngo pharynx side of the mask.

In order to insert the mask 12 into position in the laryngo pharynx LP, the holes 58,60 in hood 18 have a suitable lubricant placed therein. The mask 12 is then deformed into a shape that will enable it to be inserted through the mouth M and down into the laryngo pharynx LP. Once the mask 12 has reached the laryngo pharynx LP, it expands due to the resilience and conformability of the peripheral portion of the mask. As the peripheral portion of the mask 12 is resilient and conformable, it shapes itself such that it forms a seal with the top of the larynx L. In this fashion, ingress of extraneous fluid into the larynx L during a surgical procedure is avoided. This dramatically reduces or even avoids the risk of gastric juices or other extraneous fluids entering the larynx L and the trachea T, which would otherwise result in aspiration of the extraneous fluids into the lungs. It will be appreciated that the seal with the larynx is achieved without the mask 12 entering the larynx.

The distal end 36 of the mask 12 extends into the upper part of the esophagus O. As shown in FIG. 7, this results in the opening 40 at the distal end of mask 12 being in fluid communication with the esophagus O. Similarly, opening 42 at the proximal end of mask 12 opens into the laryngo pharynx and therefore fluid communication is provided between the esophagus and the laryngo pharynx on the laryngo pharynx side of the mask. Any gastric juices that accumulate near the upper end of the esophagus O can be removed by virtue of suction applied to one of the fluid tubes 46,48.

Figure 8:
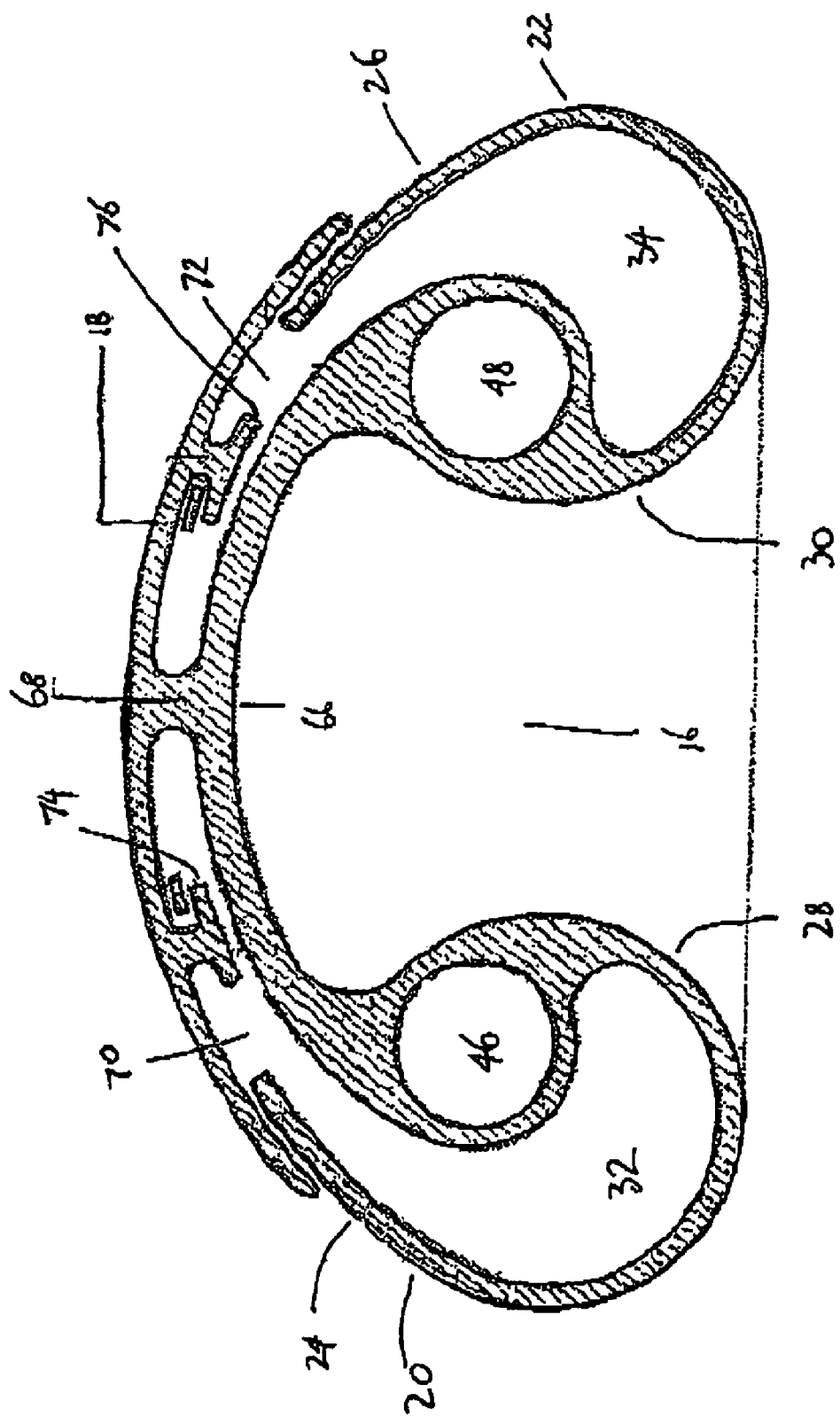
FIG. 8 is a similar cross-sectional view to that shown in FIG. 6 but of an alternative embodiment of the present invention.

FIG. 8 shows an expanded view of a slightly different embodiment of the invention to that shown in FIG. 6. For convenience, features that are common between FIG. 6 and FIG. 8 will be designated by the same reference numerals. As shown in FIG. 8, the hood 18 is connected to the floor 66 of the airway cavity 16 by connector 68. Connector 68 may be formed as an integrally formed web extending along the substantial length of the hood 18. Alternatively, the connector 68 may comprise a web or a series of separate projections that are joined to the floor 66 of airway cavity 16. Joining may be achieved by use of impulse welding, use of a suitable adhesive, or by any other suitable joining means known to those skilled in the art.

The upper wall portions 24,26 may be provided with slits 70,72 under which anchors 74,76 that are formed underneath the hood 18 can sit and engage. In this fashion, the outer extremities of the hood 18 are more securely held in position.

Figure 9:
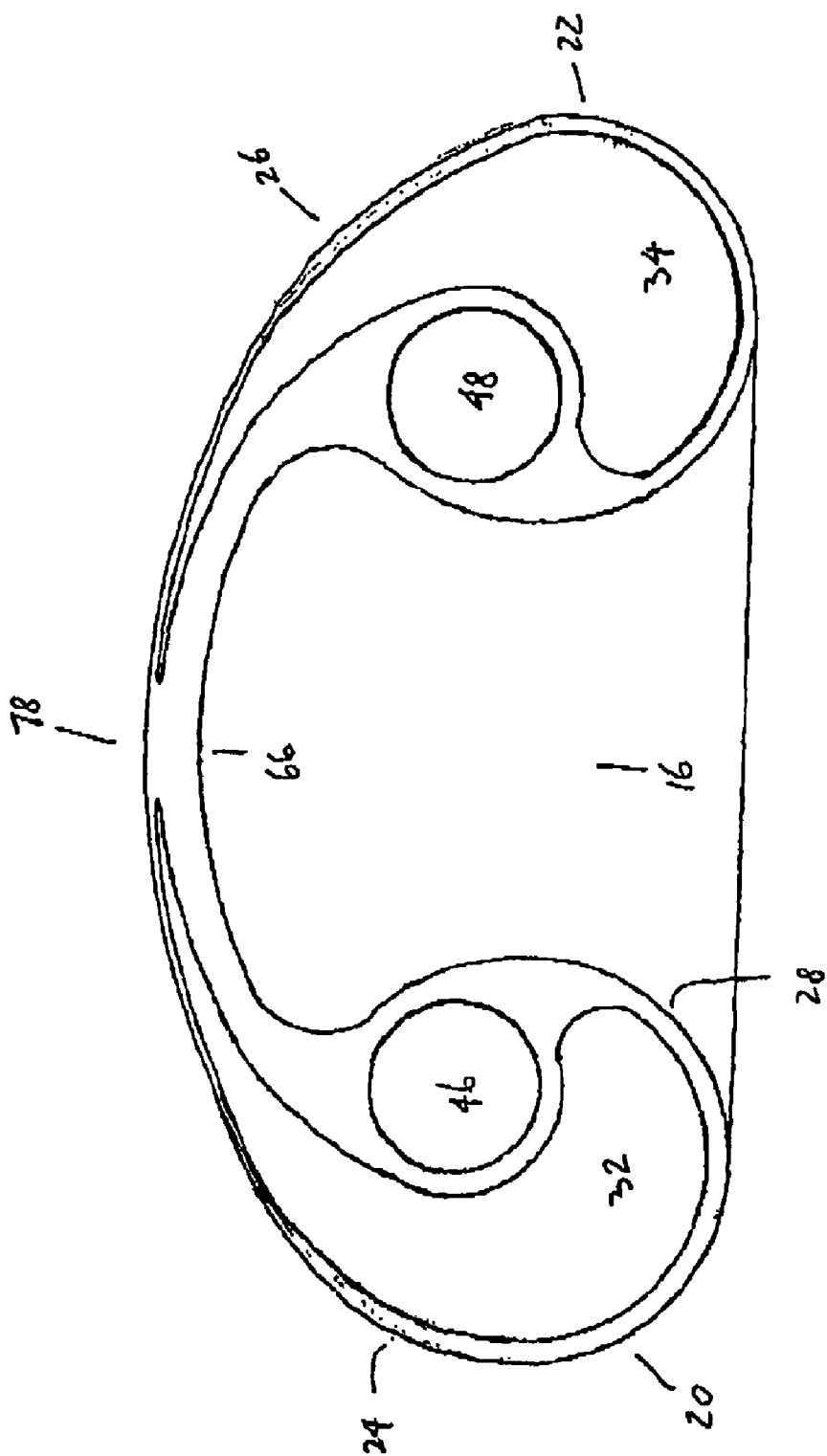
FIG. 9 shows a cross-sectional view similar to that FIG. 8 but of a further alternative embodiment of the present invention.

FIG. 9 shows a similar view to that of FIG. 8, but of a further embodiment of the present invention. For ease of convenience of description, features in FIG. 9 that are common with the features of FIG. 8 will be designated by the same reference numerals. As can be seen from FIG. 9, this embodiment differs from that of FIG. 8 in that a distinct hood is not used in the embodiment of FIG. 9.

Instead, the upper part 78 of the laryngo pharynx side of the mask is formed by extensions of wall portions 24,26 that are subsequently joined, for example, by ultrasonic welding or by use of a suitable adhesive, to the floor 66 of the airway cavity 16. Not only does this remove the need for hood 18, it also results in fluid cavities 32,34 being formed as channels. In contrast, in the embodiments shown in FIGS. 6 and 8, the fluid cavities 32,34 are partly formed by the overlap between the hood 18 and the wall portions 24,26.

FIGS. 10 and 11 shows another embodiment that is generally similar to that shown in FIG. 9. Again, features in common between FIGS. 9,10 and 11 are denoted by the same reference numerals. The main difference between the embodiment of FIG. 10 and the embodiment of FIG. 9 is that the embodiment of FIG. 10 is of a generally flatter, wider aspect ratio. A side view of the embodiment of FIG. 10 is shown in FIG. 11.

FIGS. 12 and 13 show yet a further embodiment of the present invention. For convenience, the features in FIGS. 12 and 13 that are common with the features of FIG. 10 are denoted by the same reference numerals. The embodiment of FIG. 12 differs from the embodiment of FIG. 11 in that the channels that define the fluid cavities 32,34 are formed by attaching the upper part of wall portions 24,26 to respective parts of the floor 66 of airway cavity 16 at positions located away from the centre line of the floor 66 of airway cavity 16. In particular, the end of wall portion 24 is attached to floor 66 at point 80 (in actuality, the end of wall portion 24 is attached along a line 80 to the floor of airway cavity 66). Similarly, the end of wall portion 26 is attached to the floor 66 of airway cavity 16 along the line 82. FIG. 13 clearly shows attachment line 80.

Figure 1:
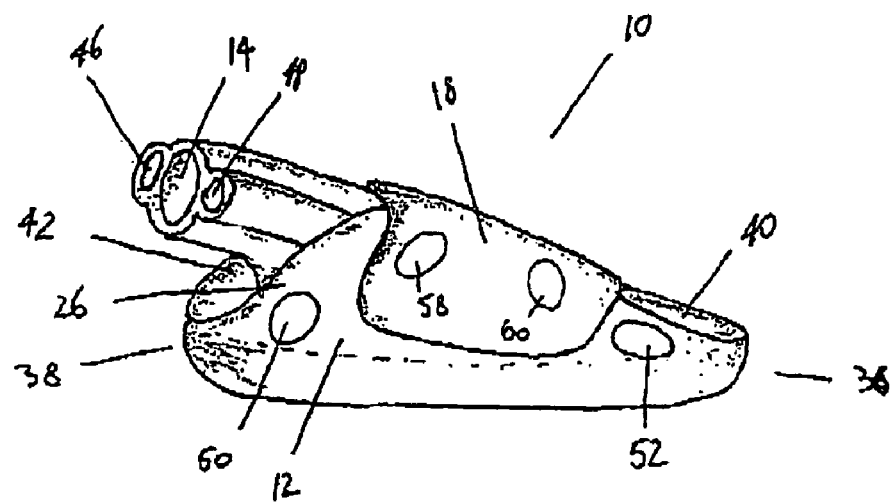
FIG. 1 is a side view of a device in accordance with the present invention.
Figure 14:
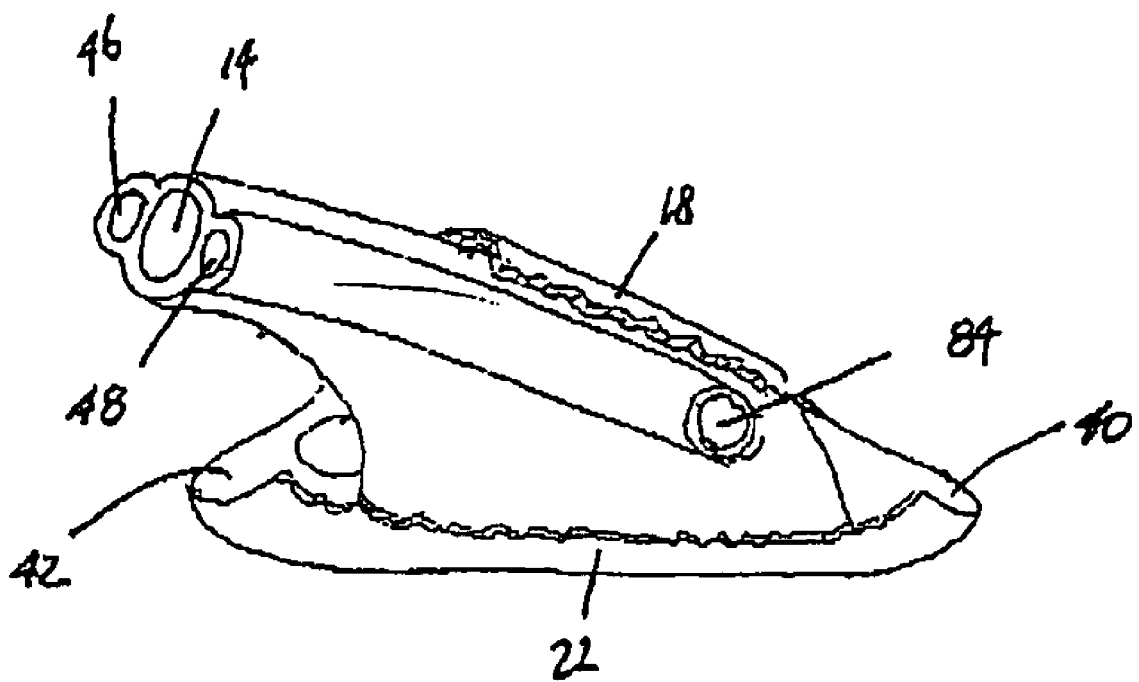
FIG. 14 is a side view, partly in cross section, of the device shown in FIG. 1.

FIG. 14 shows another view of FIG. 1 but partly in cross-section.

In particular, in FIG. 14, a part of hood 18 has been removed and a part of upturned side wall 24 and associated wall portion 26 have been removed. This allows the distal end 84 of fluid tube 48 to be clearly seen. The opening at distal end 84 of fluid tube 48 is normally positioned under upturned wall 22 and associated wall portion 26.

This allows removal of gastric fluids and other extraneous fluids from the laryngo pharynx side of the mask 12 without the risk of the distal end of the fluid tube 48 becoming blocked by tissues of the esophagus being sucked into the tube.

Similarly, FIG. 14 shows that an esophageal tube can be passed through opening 42, along one of the fluid cavities 32,34 and out of opening 40 to thereby enable an esophageal tube to be passed into the esophagus if required.

FIGS. 15 and 16 show the device 10 of the present invention in the in-use shape that is likely to be adopted when it is inserted in the laryngo pharynx space. As can be seen from these figures, the distal end proximal openings 40,42 are maintained, as are fluid cavities 32,34.

Figure 17:
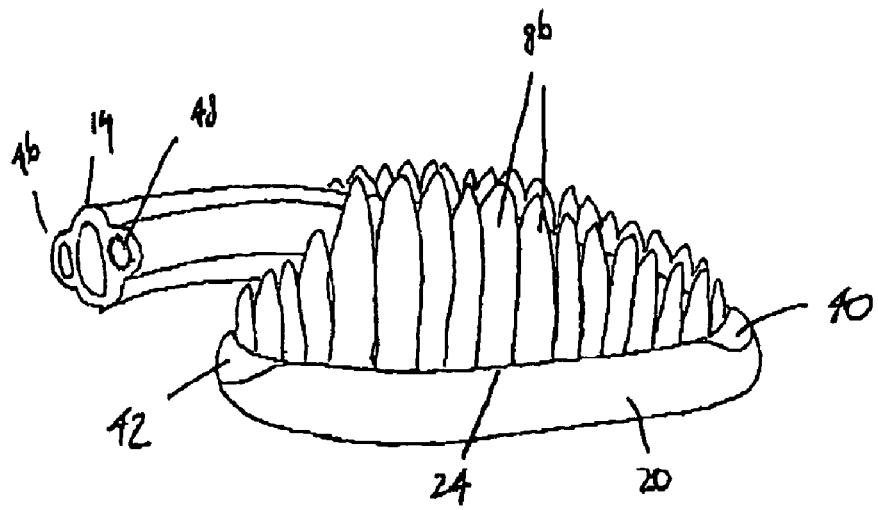
FIG. 17 is a side view of another embodiment of the present invention.
Figure 18:
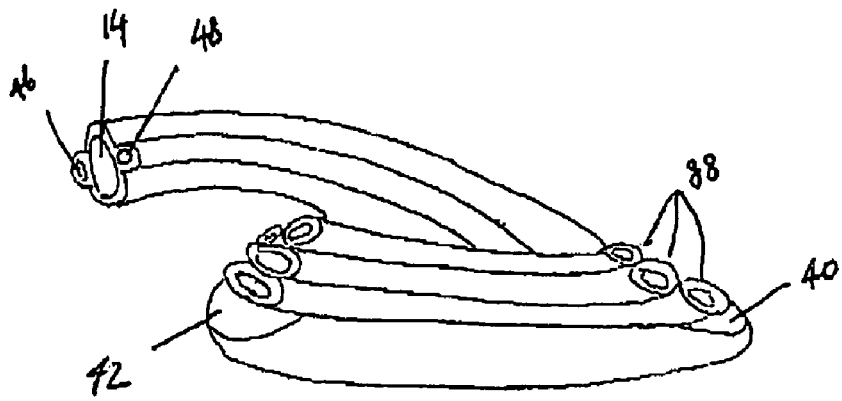
FIG. 18 is a side view of a further embodiment of the present invention.
Figure 19:
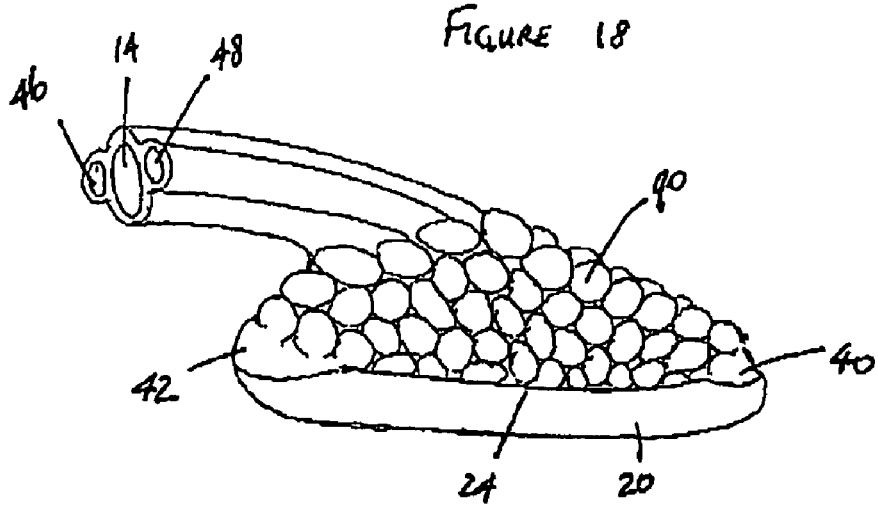
FIG. 19 is a side view of yet a further embodiment of the present invention.
Figure 21:
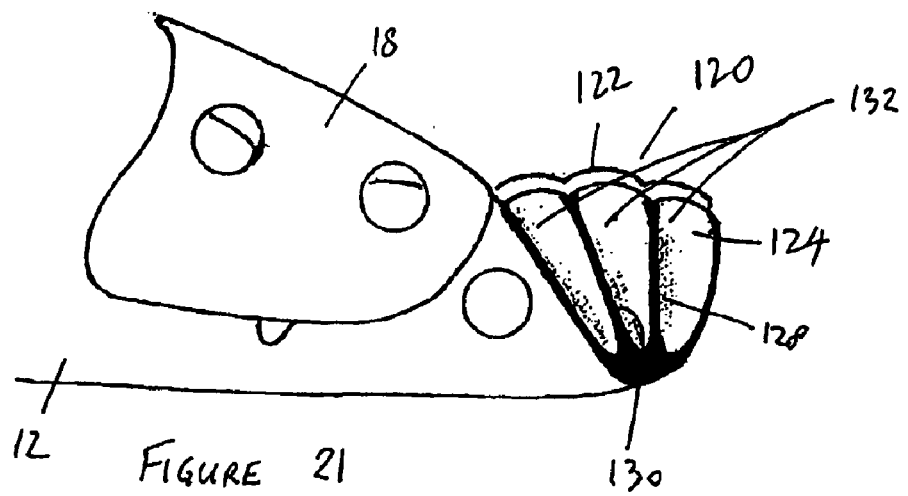
FIG. 21 is a side view of the front portion of a device in accordance with another embodiment of the invention.
Figure 22:
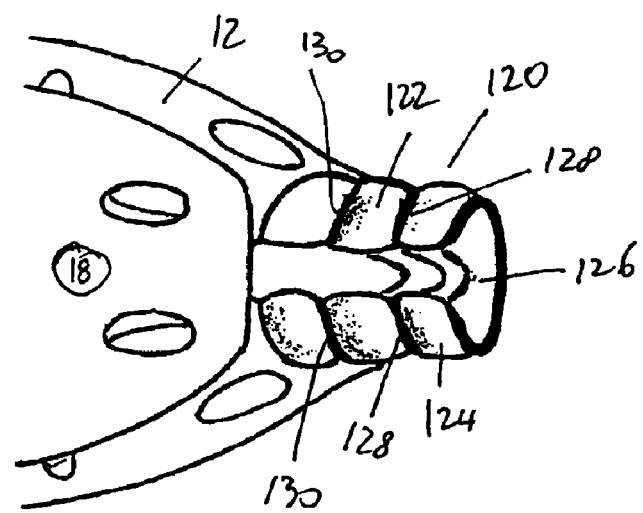
FIG. 22 is a plan view of the device of FIG. 21.

FIGS. 17 to 19 show further alternative embodiments of the present invention. In FIGS. 17 to 19, the fluid cavities 32,34 and associated openings 40, 42 are formed in the same way as described for the embodiments shown in FIGS. 1 to 16. However, the upper surface of the mask is greatly changed in FIGS. 17 to 19.

In particular, in FIG. 17, the upper side of the mask comprises a plurality of projections 86. These projections are suitably resilient and conformable to allow the mask to be inserted into the laryngo pharynx and to properly space the peripheral portion of the mask from the laryngo pharynx wall in order to ensure that a seal is achieved at the opening of the larynx. The projections 86 may, for example, be a plurality of bristles.

In FIG. 18 the upper part of the mask is formed by a number of tubular members 88. Again, these tubular members serve to properly position the peripheral portion of the mask relative to the laryngo pharynx wall.

In FIG. 19, the upper side of the mask 12 is formed by a sponge material 90.

FIGS. 21 to 30 show an alternative embodiment of the present invention which includes a longitudinally extending distal portion. This embodiment of the invention has a number of features in common with the embodiments shown in FIGS. 1 to 16. For convenience and brevity, the features in FIGS. 21 to 29 that are in common with the features of FIGS. 1 to 16 will be denoted by the same reference numeral and need not be described further.

The device of FIGS. 21 to 30 differs from the device of FIGS. 1 to 16 in that it further includes a longitudinally extending portion 120 at the distal end of the mask. It further differs from the embodiment shown in FIGS. 1 to 6 in that the hood 18 is ultrasonically welded to the roof of cavity 16.

Longitudinally extending portion comprises two side walls 122,124 (best seen in FIG. 27) that are joined by a common floor 126. Each wall 122,124 includes a series of ribs 128,130. Membrane parts 132 extend between the ribs to form the side walls.

Figure 23:
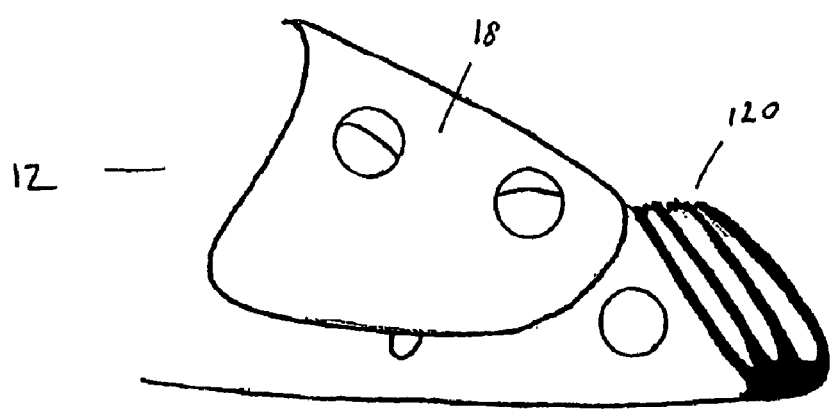
FIG. 23 is a side view of the device of FIG. 21 with the longitudinally extending portion being compressed for insertion into a patient.
Figure 24:
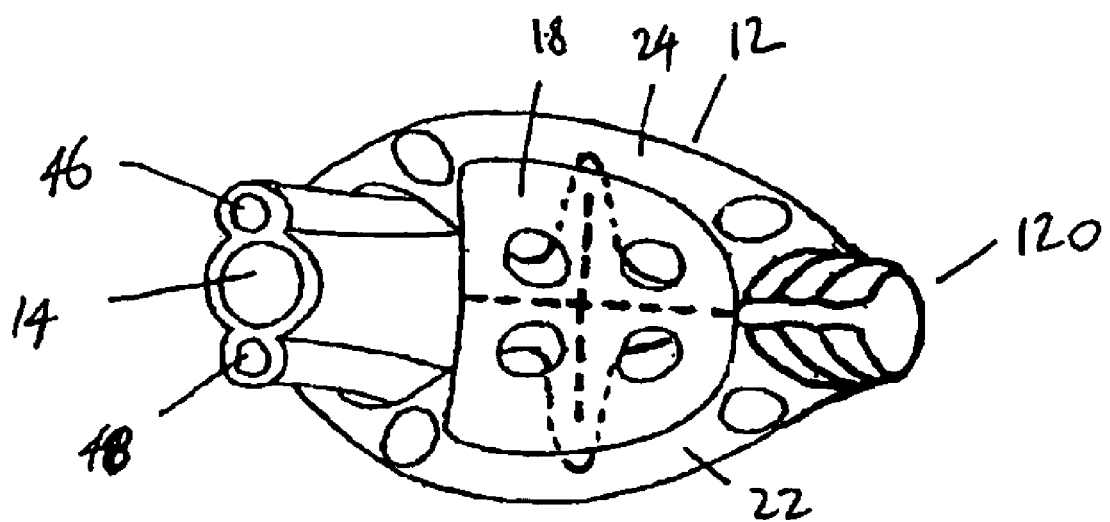
FIG. 24 is a plan view of the device of FIG. 21.
Figure 25:
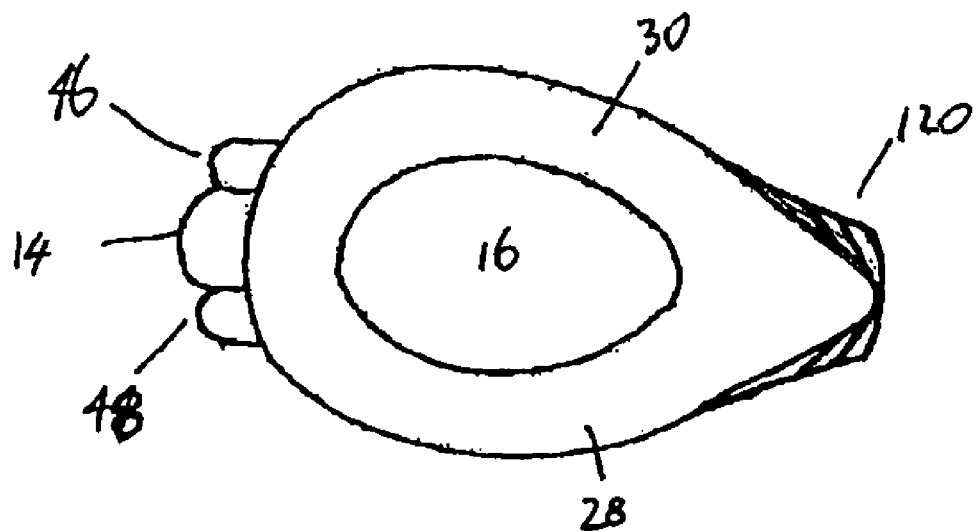
FIG. 25 is an underneath view of the device of FIG. 21.
Figure 26:
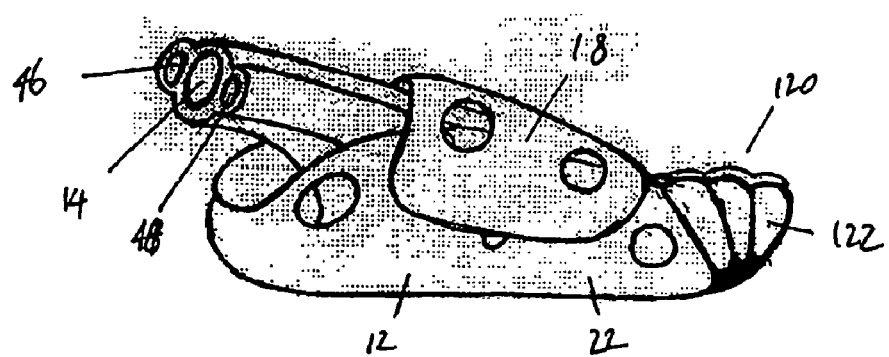
FIG. 26 is a lateral view of the entirety of the mask portion of the device of FIG. 21.
Figure 27:
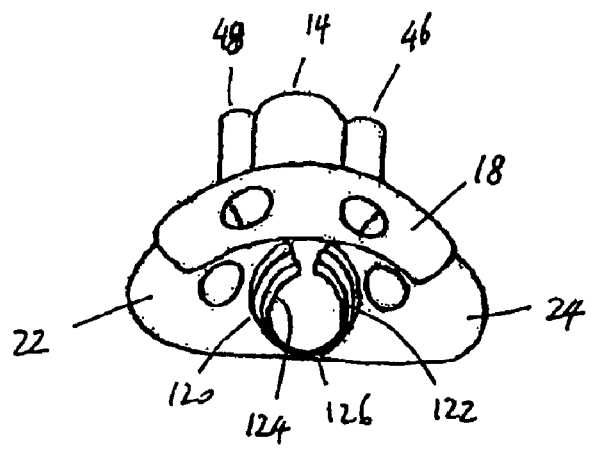
FIG. 27 is a front elevation of the device of FIG. 21.
Figure 28:
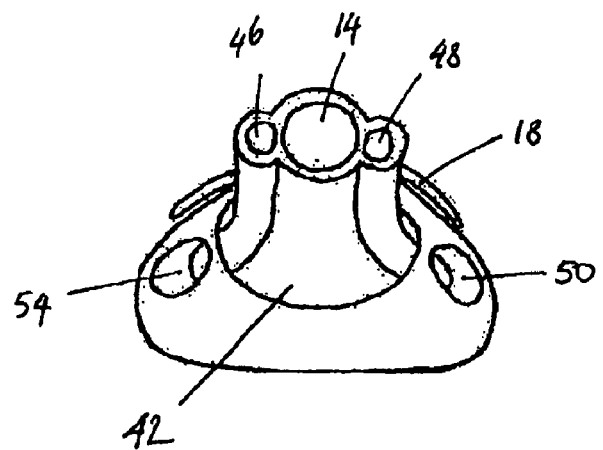
FIG. 28 is a rear elevation of the device of FIG. 21.
Figure 30:
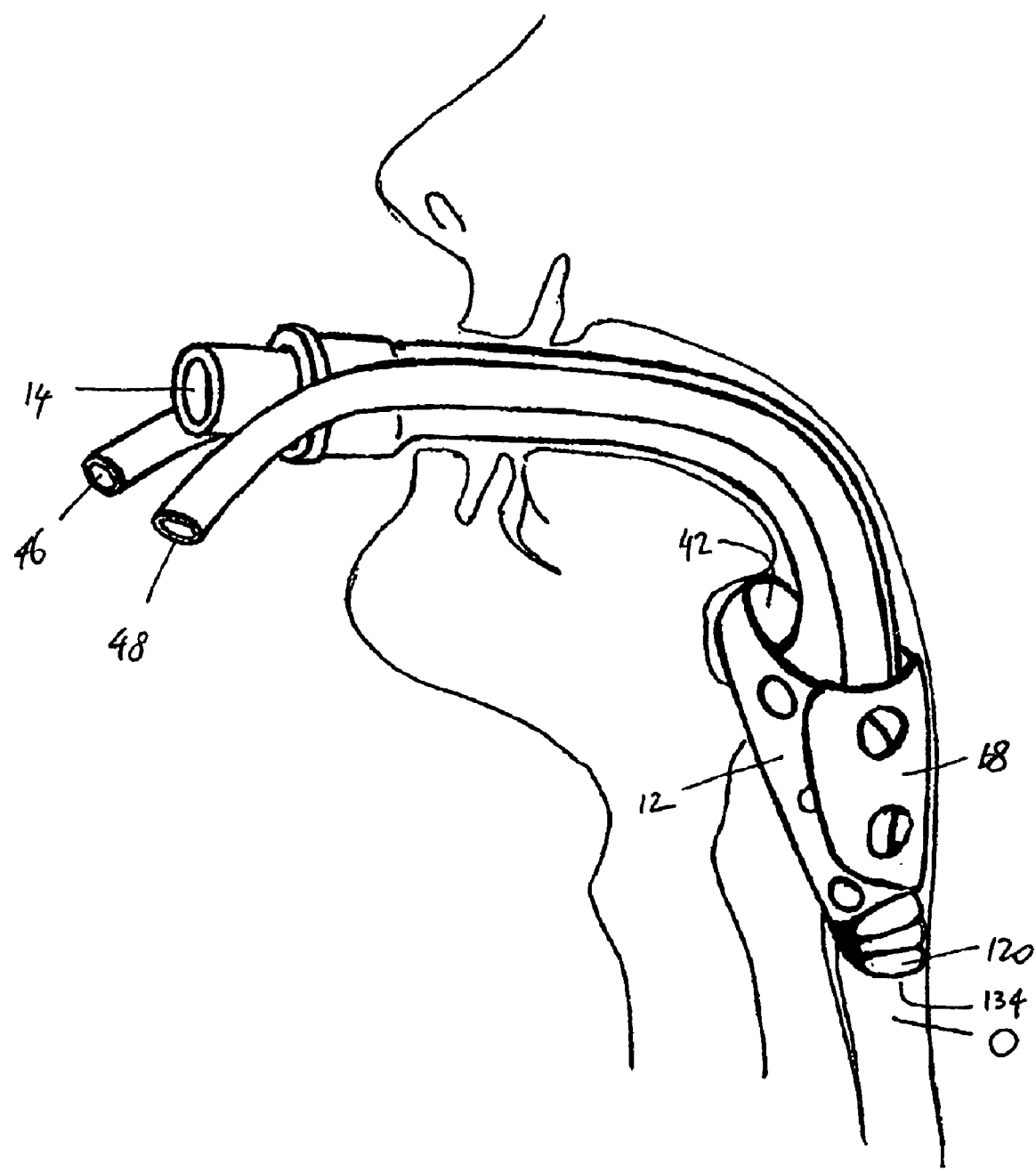
FIG. 30 is a cross-sectional view showing the device of FIG. 21 inserted into place in a patient.
Figure 31:
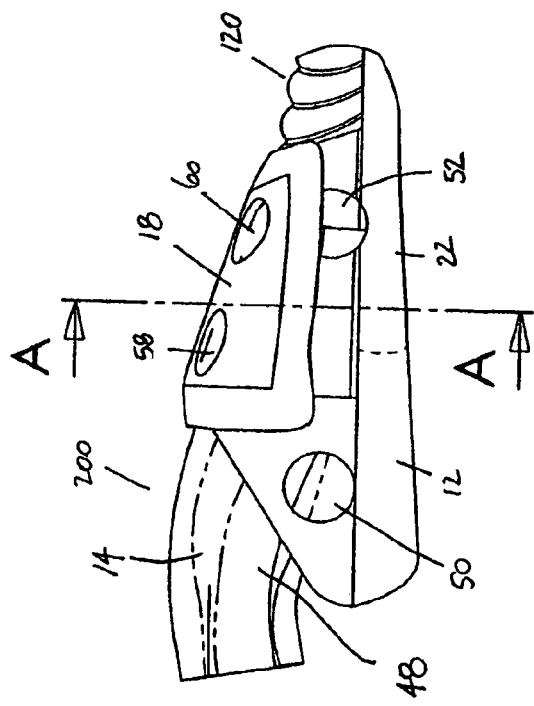
FIG. 31 is a side view of another embodiment of the present invention.
Figure 32:
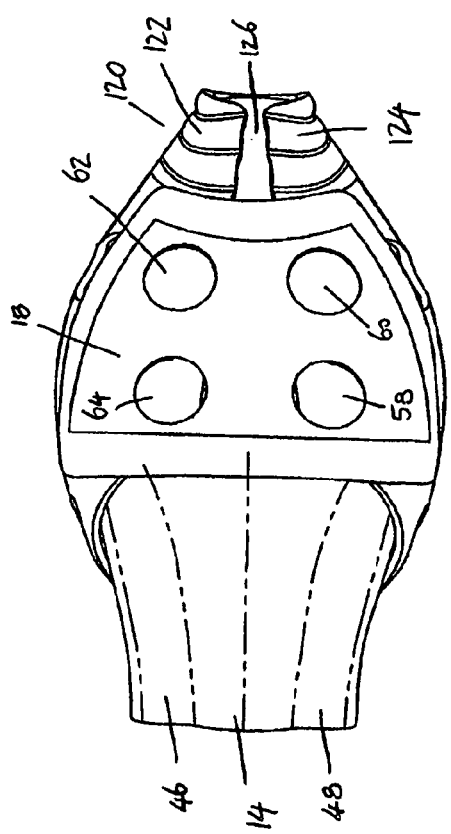
FIG. 32 is a top view of the embodiment shown in FIG. 31.
Figure 33:
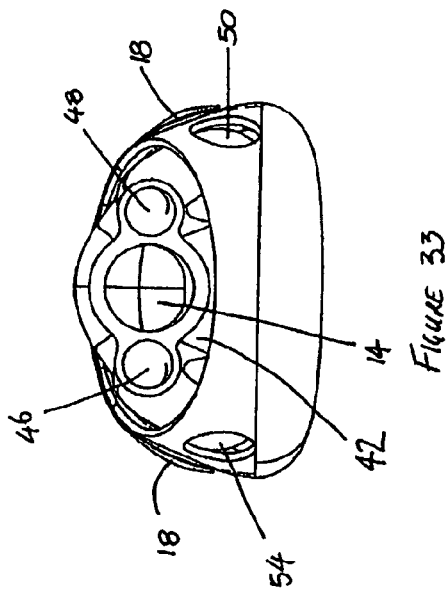
FIG. 33 is a rear view of the embodiment shown in FIG. 31.
Figure 34:
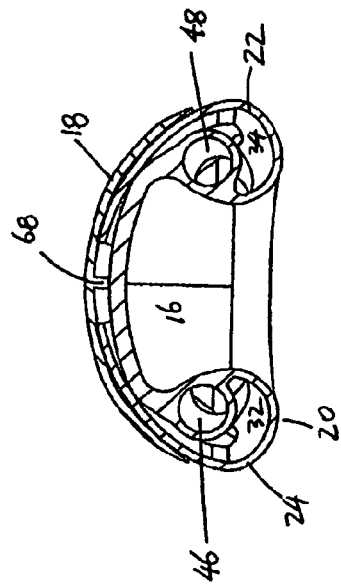
FIG. 34 is a cross sectional view taken along line A-A of FIG. 31 and looking from the rear to the front of the embodiment shown in FIG. 31.
Figure 36:
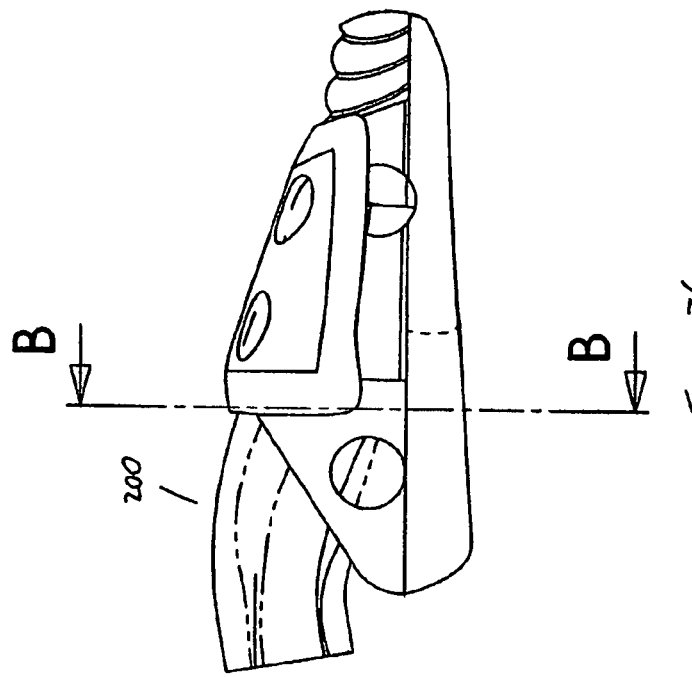
FIG. 36 is essentially the same as FIG. 31 and has been provided to show the position of section line B-B.
Figure 35:
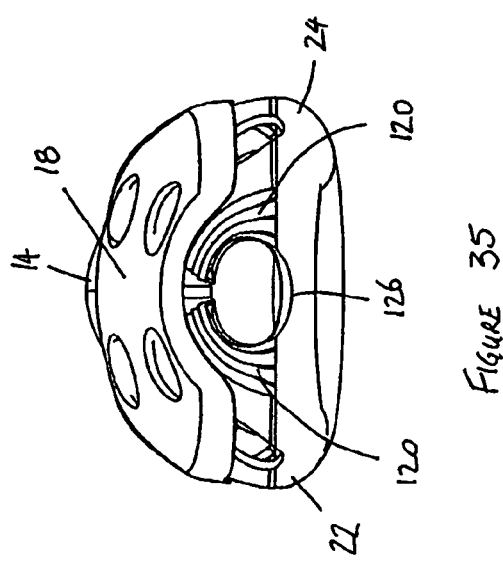
FIG. 35 is a front view of the embodiment shown in FIG. 31.
Figure 37:
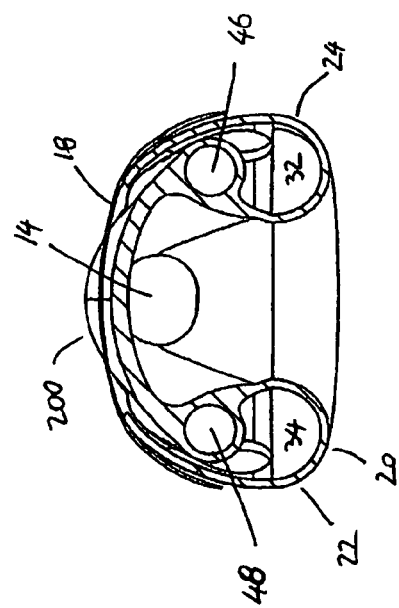
FIG. 37 is a cross sectional view taken along line B-B of FIG. 36 and looking from the front towards the rear of the mask.

The construction of side walls 122,124, in incorporating the plurality of ribs and membranes, allows the longitudinally extending portion 120 to be compressed or folded up as shown in FIG. 23 to facilitate insertion of the device into the airway of a patient. Once the device has been properly inserted, the longitudinally expanding portion 120 can expand to its expanded position. This is shown in FIG. 30. In FIG. 30, it can be seen that the longitudinally extended portion 120 extends into the upper part of esophagus O.

As can be seen in FIGS. 21 to 28, the longitudinally extending portion 120 has an open end 134. The open end 134 is in fluid communication with the cavities 32,34.

The longitudinally extending part, as shown in FIGS. 21 to 30, projects into the upper esophagus to permit improved access to any acid that may accumulate in the esophagus. The shape of the longitudinally extending portion 120 (and its resilience) also assists in keeping the opening at the distal end of the mask open, which also improves access to any acid that may build up or collect in the esophagus.

Figure 29:
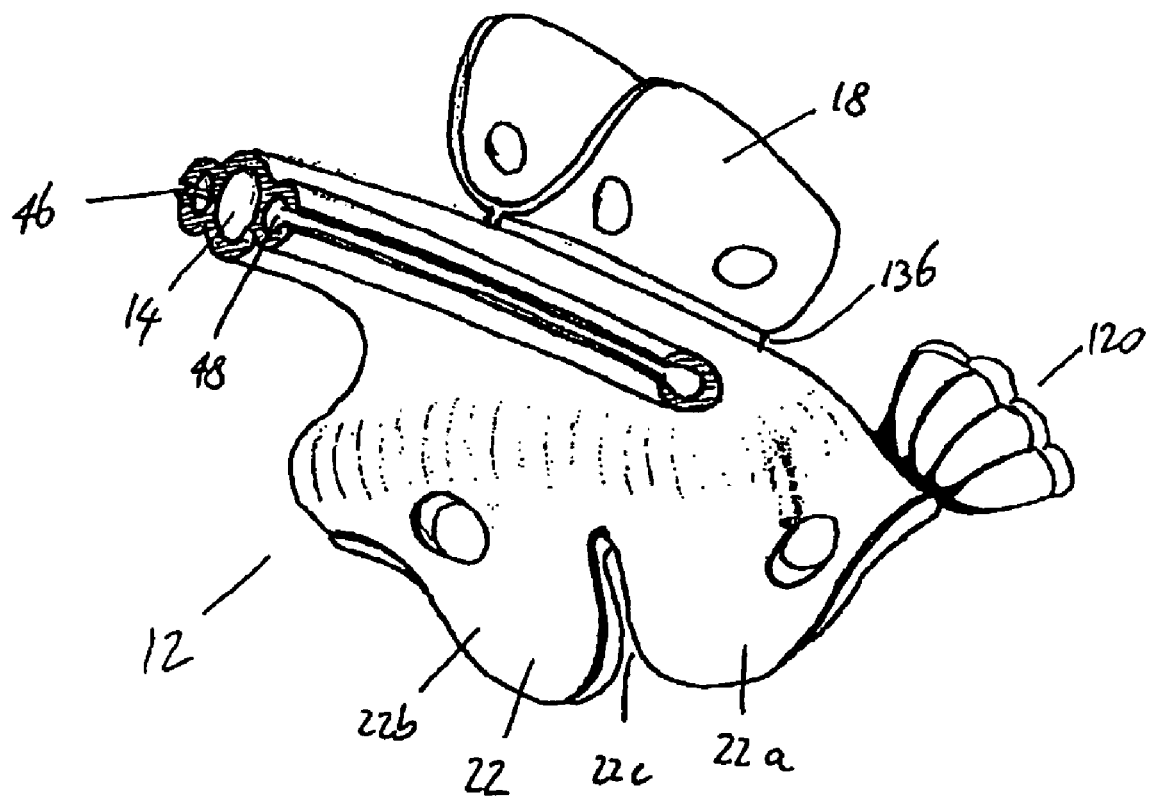
FIG. 29 is a perspective view of the device of FIG. 21 with the side walls folded downwardly and the hood folded upwardly.

FIG. 29 shows the apparatus of FIGS. 21 to 28 with the outer periphery of the mask folded down and the hood of the mask folded up. As can be seen, the floor of longitudinally extending portion 120 is joined to the upper surface of the mask 12. Similarly, the hood 18 is joined along flange 136 to the upper surface of mask 12. The wall 22 shown in FIG. 29 has been folded downwardly. As can be seen, wall 22 is formed from a butterfly shaped wall having flaps 22a and 22b separated by a gap 22c. The butterfly shape of the wall 22 allows for greater conformity of the mask to the esophagus, thereby achieving a better seal across the top of the trachea. It can also be seen that tubes 46 and 48 have a slot extending along their length for the portion. This slot was designed to make the manufacture of the tubes easily with a single die. In use the proximal positions of these slots are closed to avoid loss of suction at the distal part. The closure of the proximal part of the slot will be achieved by the covering used during attachment of the extension of the breathing tube thereto. It will be appreciated that the tubes may be manufactured with no slot and, only if needed, to have some of the distal part of the slot that is inside the cavity to be open. In use, the respective slots are positioned underneath the wall 22 (when the wall 22 is in its proper position). This slot avoids excessive suction being applied at the end point of each tube and also assists in removing any acid juices which may collect in the cavities of the mask.

The mask shown in FIGS. 21 to 30 may be subjected to several variations. In particular, the longitudinally extending part 120 is shown as having a slot or space along its upper length. It will be appreciated that the longitudinally extending part 120 may have a closed upper surface. Indeed, the longitudinally extending part may be formed from a corrugated tube which can be compressed for insertion into the patient and extended when properly inserted. The longitudinally extending part may also be attached to the mask 12 at an upper point or region. The longitudinally extending portion 120 may also be made with a series of folds in order to obtain a concertina-like action.

FIGS. 31 to 40 show various views of a laryngeal mask in accordance with a further embodiment of the present invention. The laryngeal mask shown in FIGS. 31 to 39 has a number of features in common with the laryngeal mask shown in FIGS. 21 to 29. For convenience and brevity of description, like features will be given like reference numerals and further description of those features need not be provided.

The main difference between the embodiment shown in FIGS. 31 to 39 and the embodiment shown in FIGS. 21 to 29 is that the proximal end of the mask indicated by reference numeral 200 is formed with a curvature as shown. In particular, the curvature commences at approximately the region indicated by reference numeral 200 and the airway tube 14 and suction tubes 46,48 curve generally downwardly as they extend away from the mask. This results in the overall mask having a generally lower profile than the mask shown in FIGS. 1 to 30. This results in the mask of FIGS. 31 to 39 being easier to insert into the patient. This is most clearly shown by comparing FIG. 31 with FIG. 26 and comparing FIG. 33 with FIG. 27.

In use of conventional laryngeal masks, it has been found that they can be difficult to insert into the airway as they tend to move upwardly once they pass the soft palate. In contrast, the mask shown in FIGS. 31 to 39 is much easier to insert as the curvature in the proximal end of the mask, more particularly, the curvature in the tubes exiting the proximal part of the mask, tends to move the mask into the airway once it has passed the soft palate during insertion.

Figure 38:
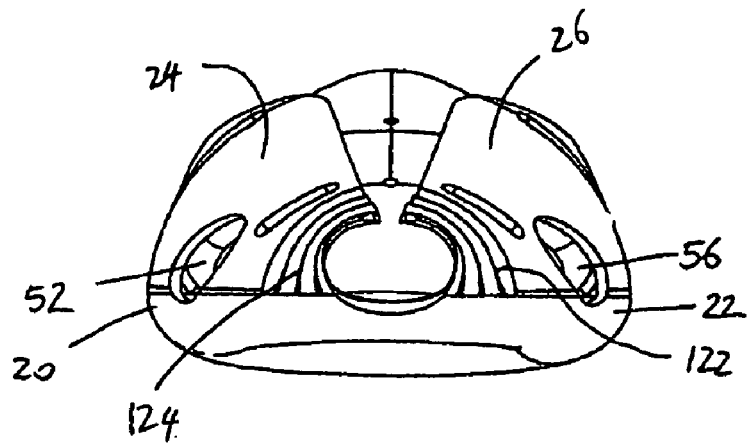
FIG. 38 is a front view of the laryngeal mask shown in FIG. 35 but with the hood removed.
Figure 39:
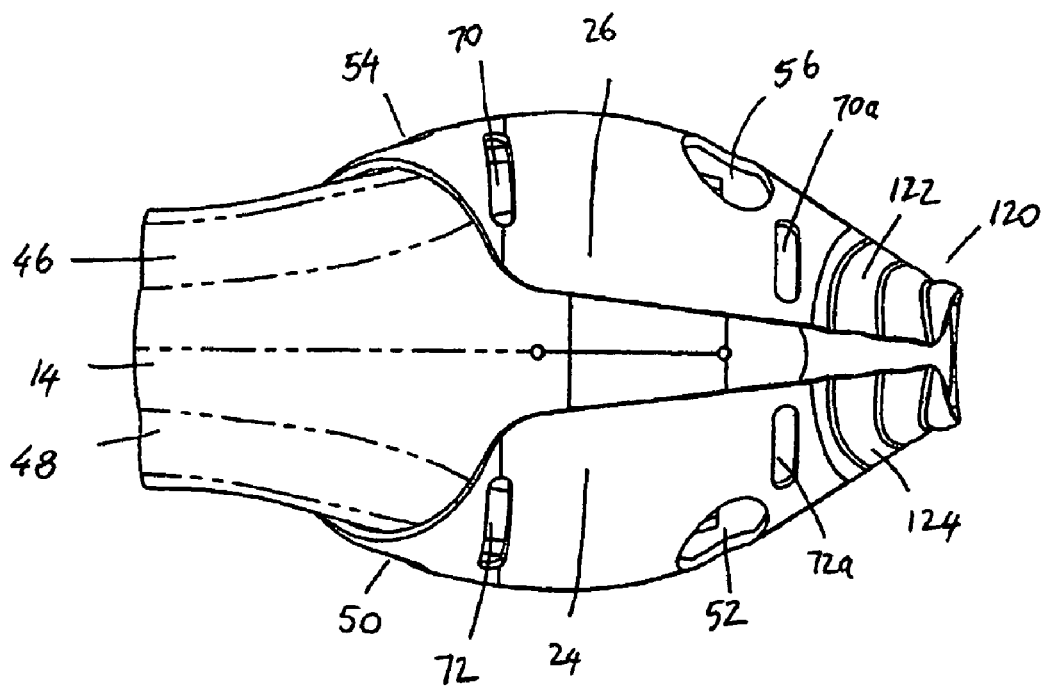
FIG. 39 is a top view of the laryngeal mask shown in FIG. 32 but with the hood removed.

FIGS. 38 and 39 also show details of the mask with the hood removed for clarity. The shape and extent of upper walls 24,26 are clearly shown in FIGS. 38 and 39, as are slots 70,70a,72,72a that assist in maintaining the hood in position.

The device in accordance with the present invention may also not have any hood and thus it will be appreciated that the hood is a preferred feature of the invention. Thus, the device shown in FIGS. 38 and 39 may be used as shown.

Figure 40:
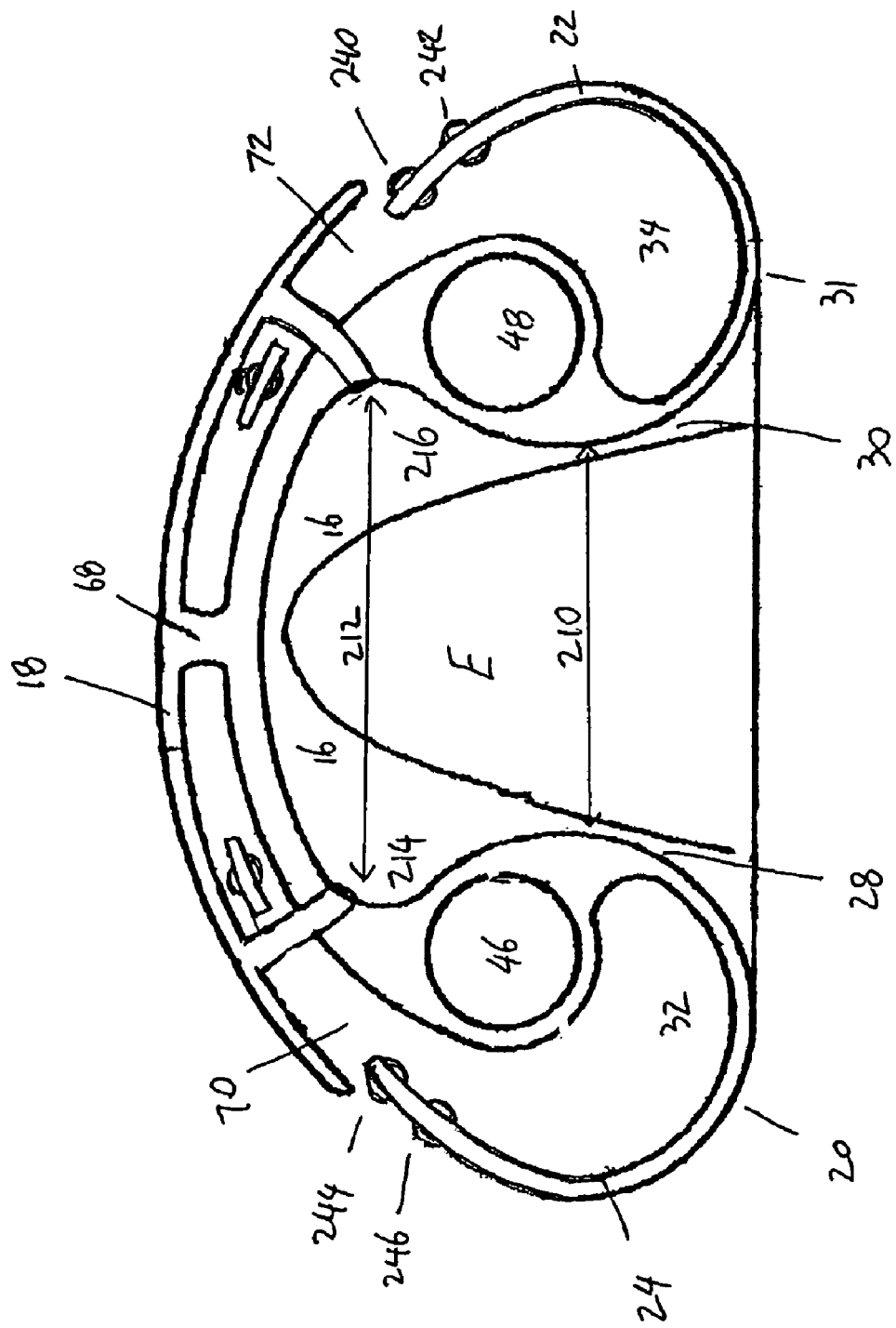
FIG. 40 is a cross-section through a laryngeal mask in accordance with another embodiment of the present invention.

FIG. 40 shows a cross-sectional view of a mask in accordance with the present invention in the inserted position. In FIG. 40, reference letter E refers to the epiglottis of the patient. Other features of the embodiment shown in FIG. 40 that are common with the embodiment shown in FIGS. 1 to 39 have been referred to by using like reference numerals to those used in FIGS. 1 to 39.

The embodiment shown in FIG. 40 includes depression 16 that opens to the laryngeal space. Depression 16 includes a region of reduced width or diameter, as shown by arrow 210 and a region of increased width or diameter, as shown by arrow 212. Thus, the shape of the depression 16 defines recesses 214,216 as shown.

Figure 41:
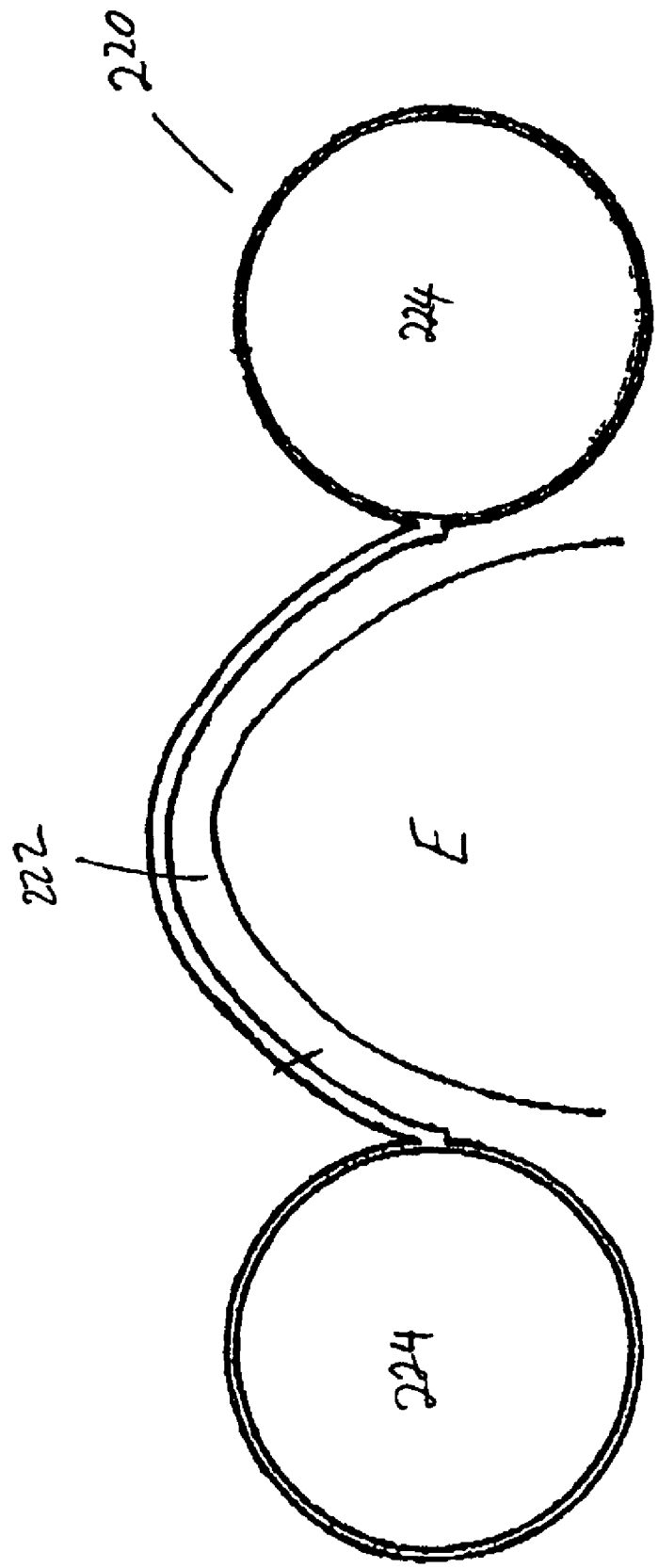
FIG. 41 is a cross-sectional view of a conventional laryngeal mask.

If the epiglottis becomes down turned, as shown by E in FIG. 40, regions 214,216 prevent airway obstruction caused by the down turned epiglottis, thereby ensuring the airway remains open. In contrast, the conventional laryngeal mask 220 as shown in FIG. 41 has a depression 222 that does not include such recesses and therefore the epiglottis E can block the airway. The conventional laryngeal mask 220 shown in FIG. 41 also includes an inflatable cuff 224.

Returning to FIG. 40, the height of the depression 16 (for example, the height of the depression ranging from 31 up to arrow 216) and the resilience of the material from which the mask is constructed results in the mask maintaining the depth of the airway cavity and maintaining the pressure against the surrounding areas of the larynx to ensure that a seal against gastric juice ingress into the larynx is obtained and to enable positive pressure ventilation of the airway to take place.

FIG. 40 also shows a number of raised projections, in particular raised semi spherical portions 240,242, 244,246. These projections minimize the contact between the upper edges of the wall portions 22,24 and the underside of the hood 18. This acts to minimize contact between the layers and ensures relative movement between the layers during insertion of the mask.

The device of the present invention has a number of advantages over commercially available competitive devices. In particular, the device of the present invention does away with the necessity of having an inflated cuff or collar to form a seal with the opening of the larynx. Instead, the device of the present invention uses a peripheral portion of the mask that is made from a resilient conformable material that is shaped to form a seal with the larynx. By avoiding the use of an inflatable cuff or collar, it is not necessary to provide a pilot tube for inflation nor to provide a one-way valve to enable inflation whilst avoiding deflation.

The device of the present invention, in including a peripheral portion that defines at least one cavity for providing fluid communication between the laryngo pharynx and the esophagus when the mask is properly inserted into the laryngo pharynx, enables fluid to flow freely between the esophagus and the laryngo pharynx. It also enables any fluid to be removed from the laryngo pharynx side of the mask. This allows the mask to be used in a fashion such that a build up of fluid around the laryngo pharynx side of the mask can be avoided, which removes the possibility of life threatening aspiration of extraneous fluids into the lungs to be avoided.

Further, unlike existing devices presently commercially available there is a continuous communication between the laryngo pharynx and the esophagus at all times. This enables the device of the present invention to cope with any gush of fluid as excess fluid can run through the fluid cavities in the mask from its distal end opening, through the fluid cavities and to the nasopharynx and to the mouth or nasal cavity. Excess fluids can then be sucked out from those areas or they can run out of the mouth or nostrils.

If high suction is applied to the suction tube, it is unlikely to become blocked by it becoming attached to the pharyngeal wall as the suction tube ends inside the fluid cavities.

The existence of a vent tube, in the form of a fluid tube that is allowed to vent to the atmosphere, keeps the cavity at atmospheric pressure at all times.

The device of the present invention is simple and cheap to manufacture and can be made with or without suction tubing or a vent.

In some embodiments of the present invention, parts of the device that come into contact with the upper part of the larynx and the laryngo pharynx wall can be made from or covered with a sponge material to reduce the pressure applied to the upper part of the larynx and the laryngo pharynx wall.

The device of the present invention can be used in a number of procedures. The device may be used during gastroscopy procedures as the gastroscope can be passed through the fluid cavity without difficulty, Esophageal stethoscopes or gastric suction tubes can also be easily passed through the fluid cavities.

In cases of poisoning or in cases of an unconscious patient where there is a need for a gastric lavage, a large bore gastric tube can be introduced and the airway of the patient successfully maintained at the same time using the device of the present invention. The device can also be used in resuscitations and positive pressure ventilation, with excess air ventilated instead of inflating the stomach through the esophagus. In all cases, the presence of the cavities in the mask providing a fluid flow path from the esophagus to the laryngo pharynx allows fluids to easily escape as the cavities provide a relatively low resistance flow path to the exterior.

The peripheral portion, at least, of the mask is made from a resilient, conformable material. Such materials have a "shape memory" property whereby if they are deformed and the deforming force removed, they attempt regain their initial shape. This shape memory property allows for easy insertion of the mask and, once inserted, allows the mask to form a seal with the opening of the larynx and to maintain the fluid cavities in an open condition. Further, as the mask expands to fill the laryngo pharyngeal space after insertion, the forces applied by the mask keeps the airway cavity in the centre of the space and opposing the larynx. This ensures that gases are properly delivered to the larynx. As a further benefit, as the opposed lateral edges of the mask push apart from each other when inserted, this places a force on the walls of the laryngo pharynx, thereby tending to centre the mask and keep it in position.

Suitable materials for use in making the mask or the peripheral portion of the mask include polyvinyl chloride, vinyl polymers, thermoplastic elastomers and other elastomers. This list is not exhaustive and the present invention encompasses the use of any suitable material that is resilient and conformable and suitable for use in medical applications.

In another embodiment, the peripheral portion may be made in the form of a concertina-type arrangement or in the form of a series of ribs, as shown in FIG. 20. In FIG. 20, which shows the lower part of the outer periphery of the mask, a series of ribs 100 are formed in the outer periphery 20. The ribs allow the shape of the outer periphery to be deformed for insertion into a patient whilst retaining the ability for the outer periphery to properly confirm to the shape of the laryngo pharynx when inserted. It will be appreciated that other shape may be used in the peripheral portion of the mask to achieve the same result and the present invention encompasses all such shapes.

It will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

What is claimed is:

1. A device adapted for maintaining an airway in a patient comprising a mask, the mask having a laryngo pharynx side, a laryngeal side and a resilient conformable peripheral portion shaped such that the mask is adapted to form a seal with the patient's larynx when the mask is positioned in the laryngo pharynx to thereby prevent ingress of extraneous fluids into the larynx, the peripheral portion of the mask defining at least two cavities having openings at a distal portion of the mask, the openings being adapted for providing fluid communication between the patient's nasopharynx and esophagus when the mask is inserted into the laryngo pharynx, and an airway tube connected to or formed with the mask for passing gas to the larynx when the mask is properly inserted into the laryngo pharynx.

2. A device as claimed in claim 1, wherein the peripheral portion of the mask comprises an upturned edge, the upturned edge defining the at least two cavities.

3. A device as claimed in claim 1, wherein the peripheral portion of the mask includes a wall portion that extends from a lateral edge of the mask away from the laryngeal side of the mask and inwardly relative to the outer edge of the mask.

4. A device as claimed in claim 3, wherein the wall portion includes a further inner portion that extends away from the lateral edge of the mask and towards the laryngeal side of the mask.

5. A device as claimed in claim 1, wherein the peripheral portion includes a fold back portion folding back over a lateral edge of the mask to thereby form the at least two cavities, the fold back portion extending along a part of at least one lateral edge of the mask.

6. A device as claimed in claim 1, wherein the at least two cavities extend along opposed edges of the mask, with the cavities formed by one or more channels formed in or forming part of the peripheral portion of the mask, wherein the one or more channels have open ends that blend into an upturned edge of the peripheral portion of the mask.

7. A device as claimed in claim 1, wherein the mask has a laryngeal side and a laryngo pharynx side and the laryngo pharynx side is provided with a contact member adapted for contacting a wall of the patient's laryngo pharynx when the mask is inserted, the contact member spacing the peripheral portion of the mask from the laryngo pharynx wall to thereby facilitate formation of a seal with the larynx.

8. A device as claimed in claim 7, wherein the contact member comprises a hood connected to or formed with the mask, wherein the hood has edges that extend over the peripheral portion of the mask, and the contact member comprises one or more projections extending away from the laryngeal side of the mask.

9. A device as claimed in claim 1, wherein the mask further includes at least one fluid tube in fluid communication with at least one of the at least two cavities, the at least one fluid tube-extending away from the mask and being adapted to remove fluids from the laryngo pharynx side of the mask, in use, wherein the at least one fluid tube has a distal outlet located within the periphery of the mask.

10. A device as claimed in claim 9, wherein the at least one fluid tube is of sufficient length to enable it to be connected to a source of vacuum or a source of venting air.

11. A device as claimed in claim 1, wherein the mask further includes an airway tube connected to or formed with the mask for passing gas to the larynx when the mask is inserted into the laryngo pharynx, wherein the laryngeal side of the mask defines a depression and the airway tube is in fluid communication with the depression.

12. A device as claimed in claim 11, wherein the depression on the laryngeal side of the mask is defined by an inner wall of the mask and the inner wall has a region of relative increased width and a region of relative decreased width such that the region of relative increased width defines a recess in the depression when the mask is inserted, the recess providing a region of clearance between the inner wall and the epiglottis of the patient.

13. A device as claimed in claim 11, wherein the depression on the laryngeal side of the mask is defined by an inner wall of the mask and the inner wall of the mask is arranged to facilitate maintenance of the depth of the airway depression and to maintain pressure against the surrounding areas of the larynx to maintain the seal against ingress of gastric juices into the larynx and to allow positive pressure ventilation of the airway.

14. A device as claimed in claim 1, wherein the distal portion of the mask includes a longitudinally extending portion that, in use, is adapted to extend into the esophagus, the longitudinally extending portion being in fluid communication with the at least two cavities and extending into an upper portion of the esophagus.

15. A device as claimed in claim 14, wherein the longitudinally extending portion is shaped to bias a distal end of the at least two cavities to an open position and comprises a tubular portion defining a passageway having an opening along one wall thereof.

16. A device as claimed in claim 14, wherein the longitudinally extending portion comprises a portion that can be folded up or collapsed to facilitate insertion of the mask into a patient and to move to an expanded position once inserted.

17. A device as claimed in claim 14, wherein the longitudinally extending portion is a longitudinal extension of the peripheral portion of the mask and proximal tubing of the mask is shaped to have a curvature extending from near the proximal end of the mask and in a direction away from the mask.

18. A device adapted for maintaining an airway in a patient comprising a mask, the mask having a resilient conformable peripheral portion shaped such that the mask is adapted to form a seal with the larynx when the mask is positioned in the patient's laryngo pharynx to thereby prevent ingress of extraneous fluids into the larynx, a pair of cavities extending at or near the lateral periphery of the mask and having openings at a distal portion of the mask, the openings being adapted for providing fluid communication between the patient's nasopharynx and-esophagus when the mask is inserted into the laryngo pharynx, and an airway tube connected to or formed with the mask for passing gas to the larynx when the mask is properly inserted into the laryngo pharynx.

19. A device as claimed in claim 1, wherein the at least two cavities are adapted for providing fluid communication between the patient's nasopharynx and esophagus.

20. A device adapted for maintaining an airway in a patient comprising a mask, the mask having a laryngo pharynx side, a laryngeal side and a resilient conformable peripheral portion shaped such that the mask is adapted to form a seal with the patient's larynx when the mask is positioned in the laryngo pharynx to thereby prevent ingress of extraneous fluids into the larynx, the mask defining at least two cavities having openings at a distal portion of the mask, the openings being adapted for providing fluid communication between the patient's nasopharynx and-esophagus when the mask is inserted into the laryngo pharynx, and an airway tube connected to or formed with the mask for passing gas to the larynx when the mask is properly inserted into the laryngo pharynx.

21. A device as claimed in claim 20, wherein the distal portion of the mask includes a longitudinally extending portion that, in use, is adapted to extend into the esophagus, the longitudinally extending portion being in fluid communication with the at least two cavities and extending into an upper portion of the esophagus.

22. A device as claimed in claim 21, wherein the longitudinally extending portion is shaped to bias a distal end of the at least two cavities to an open position and comprises a tubular portion defining a passageway having an opening along one wall thereof.

23. A device as claimed in claim 22, wherein the longitudinally extending portion comprises a portion that can be folded up or collapsed to facilitate insertion of the mask into a patient and to move to an expanded position once inserted.

24. A device as claimed in claim 23, wherein the longitudinally extending portion includes a plurality of ribs, a corrugated tube or a plurality of fold lines.

25. A device as claimed in claim 16, wherein the longitudinally extending portion includes a plurality of ribs, a corrugated tube or a plurality of fold lines.

* * * * *